US011638636B2

(12) United States Patent
Oren-Artzi et al.

(10) Patent No.: US 11,638,636 B2
(45) Date of Patent: May 2, 2023

(54) SYSTEMS AND METHODS FOR REMOTE DENTAL MONITORING

(71) Applicant: Get-Grin Inc., Airmont, NY (US)

(72) Inventors: Pamela Sharon Oren-Artzi, Austin, TX (US); Alon Luis Lipnik, Tel Aviv (IL); Adam Benjamin Schulhof, New City, NY (US)

(73) Assignee: GET GRIN INC., Airmont, NY (US)

( * ) Notice: Subject to any disclaimer, the term of this patent is extended or adjusted under 35 U.S.C. 154(b) by 0 days.

(21) Appl. No.: 17/336,997

(22) Filed: Jun. 2, 2021

(65) Prior Publication Data

US 2021/0282634 A1    Sep. 16, 2021

Related U.S. Application Data

(63) Continuation of application No. PCT/US2021/019722, filed on Feb. 25, 2021.
(Continued)

(51) Int. Cl.
*A61C 19/04*    (2006.01)
*A61B 5/00*    (2006.01)
(Continued)

(52) U.S. Cl.
CPC .......... *A61C 19/04* (2013.01); *A61B 1/00009* (2013.01); *A61B 1/00194* (2022.02);
(Continued)

(58) Field of Classification Search
None
See application file for complete search history.

(56) References Cited

U.S. PATENT DOCUMENTS 3,971,954 A * 7/1976 Kleinberg ............ A61B 5/0088
250/475.2
6,947,038 B1    9/2005 Anh et al.
(Continued)

FOREIGN PATENT DOCUMENTS

DE    202015102709 U1    8/2015
EP    1252858 A2 * 10/2002    ......... A61B 1/00041
(Continued)

OTHER PUBLICATIONS

PCT/US2021/019722 International Search Report and Written Opinion dated May 6, 2021.
(Continued)

*Primary Examiner* — John P Leubecker
(74) *Attorney, Agent, or Firm* — Wilson Sonsini Goodrich & Rosati

(57) ABSTRACT

An intraoral imaging system comprising an intraoral adapter. The intraoral adapter may be operably coupled to a mobile device. The intraoral adapter may comprise an elongated housing comprising a viewing channel. The viewing channel may define a field of view of an intraoral region of a subject's mouth for intraoral scanning using a camera of a mobile device. The elongated housing may comprise a flange that is positioned outside of the field of view of the intraoral region of the subject's mouth. The intraoral imaging system may further comprise an image processing unit configured to (i) process a plurality of intraoral images and/or videos captured using the camera of the mobile device, and (ii) determine a dental condition of the subject based at least in part on the plurality of intraoral images and/or videos.

29 Claims, 20 Drawing Sheets

Related U.S. Application Data

(60) Provisional application No. 62/981,747, filed on Feb. 26, 2020.

(51) Int. Cl.
*A61B 1/247* (2006.01)
*A61B 1/24* (2006.01)
*A61C 19/00* (2006.01)
*A61B 1/04* (2006.01)
*A61B 1/00* (2006.01)

(52) U.S. Cl.
CPC ............... *A61B 1/042* (2013.01); *A61B 1/24* (2013.01); *A61B 1/247* (2013.01); *A61B 5/682* (2013.01); *A61B 5/6898* (2013.01); *A61C 19/00* (2013.01); *A61B 1/00011* (2013.01); *A61B 1/00105* (2013.01); *A61B 2560/0443* (2013.01)

(56) References Cited

U.S. PATENT DOCUMENTS

| | | |
|---|---|---|
| 7,077,647 B2 | 7/2006 | Choi et al. |
| 7,184,150 B2 | 2/2007 | Quadling et al. |
| 7,625,335 B2 | 12/2009 | Deichmann et al. |
| 7,912,673 B2 | 3/2011 | Hebert et al. |
| 8,562,338 B2 | 10/2013 | Kitching et al. |
| 8,998,609 B2 | 4/2015 | Prakash et al. |
| 9,168,113 B2 | 10/2015 | Wu et al. |
| 9,324,190 B2 | 4/2016 | Bell et al. |
| 9,329,675 B2 | 5/2016 | Ojelund et al. |
| 9,439,568 B2 | 9/2016 | Atiya et al. |
| D774,193 S | 12/2016 | Makmel et al. |
| 9,510,757 B2 | 12/2016 | Kopelman et al. |
| 9,788,917 B2 | 10/2017 | Mah |
| 9,808,148 B2 | 11/2017 | Miller et al. |
| D806,248 S | 12/2017 | Makmel et al. |
| D827,137 S | 8/2018 | Miller |
| 10,108,269 B2 | 10/2018 | Sabina et al. |
| 10,123,706 B2 | 11/2018 | Elbaz et al. |
| 10,206,759 B2 | 2/2019 | Salah et al. |
| 10,342,645 B2 | 7/2019 | Salah et al. |
| 10,357,342 B2 | 7/2019 | Falkel |
| 10,410,430 B2 | 9/2019 | Somasundaram et al. |
| 10,417,774 B2 | 9/2019 | Salah et al. |
| 10,485,638 B2 | 11/2019 | Salah et al. |
| 10,492,893 B2 | 12/2019 | Van Der Poel et al. |
| 10,588,501 B2 | 3/2020 | Salah et al. |
| 10,588,723 B2 | 3/2020 | Falkel |
| 10,595,966 B2 | 3/2020 | Carrier, Jr. et al. |
| 10,636,522 B2 | 4/2020 | Katzman et al. |
| 10,685,259 B2 | 6/2020 | Salah et al. |
| 10,736,715 B2 | 8/2020 | Salah et al. |
| 10,755,409 B2 | 8/2020 | Salah et al. |
| 10,779,718 B2 | 9/2020 | Meyer et al. |
| 10,779,909 B2 | 9/2020 | Salah et al. |
| 10,799,321 B2 | 10/2020 | Salah et al. |
| 10,803,146 B2 | 10/2020 | Cosse |
| 10,842,592 B2 | 11/2020 | Salah et al. |
| 10,849,723 B1 | 12/2020 | Yancey et al. |
| D910,850 S | 2/2021 | Hansen et al. |
| 10,925,698 B2 | 2/2021 | Falkel |
| 10,932,885 B2 | 3/2021 | Carrier, Jr. et al. |
| 10,966,667 B2 | 4/2021 | Salah et al. |
| 11,013,578 B2 | 5/2021 | Salah |
| 11,049,248 B2 | 6/2021 | Salah et al. |
| D925,739 S | 7/2021 | Shalev et al. |
| 11,083,551 B2 | 8/2021 | Yancey et al. |
| 11,107,218 B2 | 8/2021 | Salah et al. |
| 11,109,945 B2 | 9/2021 | Salah et al. |
| 11,191,617 B2 | 12/2021 | Carrier, Jr. et al. |
| 11,246,688 B2 | 2/2022 | Salah et al. |
| 11,270,523 B2 | 3/2022 | Long et al. |
| 11,392,210 B2 | 7/2022 | Sabina et al. |
| D962,437 S | 8/2022 | Oren-Artzi et al. |
| 2002/0196438 A1* | 12/2002 | Kerschbaumer .......... G01J 3/50 356/327 |
| 2003/0148243 A1* | 8/2003 | Kerschbaumer ... A61B 1/00052 433/29 |
| 2004/0252303 A1 | 12/2004 | Giorgianni et al. |
| 2006/0001739 A1 | 1/2006 | Babayoff |
| 2006/0029903 A1* | 2/2006 | Kobayashi ............... A61B 1/24 433/29 |
| 2006/0040230 A1 | 2/2006 | Blanding et al. |
| 2008/0172386 A1 | 7/2008 | Ammar et al. |
| 2008/0309924 A1 | 12/2008 | Jung et al. |
| 2009/0076321 A1 | 3/2009 | Suyama et al. |
| 2013/0209954 A1* | 8/2013 | Prakash .................. A61B 1/042 433/29 |
| 2015/0029309 A1 | 1/2015 | Michaeli et al. |
| 2015/0118638 A1 | 4/2015 | Cowburn |
| 2018/0125610 A1* | 5/2018 | Carrier, Jr. ............ G06V 10/764 |
| 2018/0160887 A1* | 6/2018 | Hefez ................ A61B 1/00052 |
| 2018/0174367 A1 | 6/2018 | Marom et al. |
| 2018/0185125 A1 | 7/2018 | Salah et al. |
| 2018/0192964 A1 | 7/2018 | Stalder et al. |
| 2018/0228359 A1* | 8/2018 | Meyer ........................ G06T 7/70 |
| 2018/0263730 A1 | 9/2018 | Sirovskiy et al. |
| 2018/0284580 A1 | 10/2018 | Matthews |
| 2018/0296080 A1* | 10/2018 | Glinec ................ G01B 11/2518 |
| 2018/0303331 A1* | 10/2018 | Salah ................ A61B 5/1032 |
| 2018/0303580 A1* | 10/2018 | Salah ........................ A61C 5/90 |
| 2018/0344430 A1 | 12/2018 | Salah et al. |
| 2019/0026598 A1 | 1/2019 | Salah et al. |
| 2019/0026599 A1 | 1/2019 | Salah et al. |
| 2019/0125493 A1 | 5/2019 | Salah et al. |
| 2019/0133717 A1 | 5/2019 | Salah et al. |
| 2019/0167115 A1* | 6/2019 | Dorodvand .......... A61B 5/4552 |
| 2019/0200903 A1 | 7/2019 | Watson |
| 2019/0269485 A1 | 9/2019 | Elbaz et al. |
| 2019/0289283 A1 | 9/2019 | Fisker et al. |
| 2019/0307531 A1 | 10/2019 | Wu et al. |
| 2019/0313963 A1 | 10/2019 | Hillen |
| 2019/0328489 A1 | 10/2019 | Capron-Richard et al. |
| 2020/0297205 A1* | 9/2020 | Hill ........................... A61B 1/32 |
| 2020/0334813 A1 | 10/2020 | Salah et al. |
| 2020/0404243 A1 | 12/2020 | Saphier et al. |
| 2020/0405447 A1 | 12/2020 | Salah et al. |
| 2021/0007834 A1 | 1/2021 | Salah et al. |
| 2021/0045858 A1 | 2/2021 | Salah et al. |
| 2021/0052138 A1* | 2/2021 | Bevis ....................... G16H 30/20 |
| 2021/0106229 A1 | 4/2021 | Van Der Poel et al. |
| 2021/0145550 A1 | 5/2021 | Salah et al. |
| 2021/0158614 A1 | 5/2021 | Katzman et al. |
| 2021/0161621 A1 | 6/2021 | Salah et al. |
| 2021/0186658 A1 | 6/2021 | Salah et al. |
| 2021/0192724 A1 | 6/2021 | Salah et al. |
| 2021/0244502 A1* | 8/2021 | Farkash ................ A61B 5/0088 |
| 2021/0259807 A1 | 8/2021 | Salah et al. |
| 2021/0361387 A1 | 11/2021 | Salah et al. |
| 2021/0366119 A1 | 11/2021 | Salah et al. |
| 2021/0390687 A1 | 12/2021 | Salah et al. |

FOREIGN PATENT DOCUMENTS

| | | |
|---|---|---|
| JP | 4576325 B2 | 11/2010 |
| JP | 2018134418 A | 8/2018 |
| TW | M503883 U | 7/2015 |
| WO | WO-2012038474 A1 | 3/2012 |
| WO | WO-2016185463 A1 | 11/2016 |
| WO | WO-2018080413 A2 | 5/2018 |
| WO | WO-2019149700 A1 | 8/2019 |
| WO | WO-2019215129 A1 | 11/2019 |
| WO | WO-2019224055 A1 | 11/2019 |
| WO | WO-2020011863 A1 | 1/2020 |
| WO | WO-2020011864 A1 | 1/2020 |
| WO | WO-2020089248 A1 | 5/2020 |
| WO | WO-2020185733 A1 | 9/2020 |
| WO | WO-2021058930 A1 | 4/2021 |
| WO | WO-2021173867 A1 | 9/2021 |
| WO | WO-2021236616 A1 | 11/2021 |

(56) References Cited

OTHER PUBLICATIONS

Co-pending U.S. Appl. No. 29/731,805, inventors Oren-Artzi; Pamela Sharon et al., filed Apr. 17, 2020.
Co-pending U.S. Appl. No. 29/734,658, inventors Oren-Artzi; Pamela Sharon et al., filed May 14, 2020.
Co-pending U.S. Appl. No. 29/758,330, inventors Oren-Artzi; Pamela Sharon et al., filed Nov. 13, 2020.
PCT/US2021/032932 International Search Report and Written Opinion dated Sep. 9, 2021.
U.S. Appl. No. 29/734,658 Office Action dated Oct. 21, 2021.
U.S. Appl. No. 29/758,330 Office Action dated Jan. 10, 2022.
Co-pending U.S. Appl. No. D29/865,561, inventors Oren-Artzi; Pamela Sharon et al., filed Aug. 1, 2022.
PCT/US2022/035176 International Search Report and Written Opinion dated Sep. 15, 2022.
PCT/US2022/038736 International Search Report and Written Opinion dated Nov. 1, 2022.
PCT/US2022/040265 International Search Report and Written Opinion dated Nov. 3, 2022.
U.S. Appl. No. 29/758,330 Notice of Allowance dated Apr. 28, 2022.

\* cited by examiner

SYSTEMS AND METHODS FOR REMOTE DENTAL MONITORING

CROSS REFERENCE

This application is a continuation of International Patent Application No. PCT/US21/19722, filed Feb. 25, 2021, which claims the benefit of U.S. Provisional Application No. 62/981,747 filed Feb. 26, 2020, each of which is incorporated herein by reference in its entirety for all purposes.

BACKGROUND

Dental professionals and orthodontists may treat and monitor a patient's dental condition based on in-person visits. Treatment and monitoring of a patient's dental condition may require a patient to schedule multiple in-person visits to a dentist or orthodontist. The quality of treatment and the accuracy of monitoring may vary depending on how often and how consistently a patient sees a dentist or orthodontist. In some cases, suboptimal treatment outcomes may result if a patient is unable or unwilling to schedule regular visits to a dentist or orthodontist.

SUMMARY

Recognized herein is a need for remote dental monitoring solutions to allow dental patients to receive high quality dental care, without requiring a dental professional to be physically present with the patient. Some dental professionals and orthodontists may use conventional teledentistry solutions to accommodate patients' needs and schedules. However, such conventional teledentistry solutions may provide inadequate levels of supervision. Further, such conventional teledentistry solutions may be limited by an inaccurate or insufficient monitoring of a patient's dental condition based on one or more photos taken by the patient, if the photos do not adequately capture various intraoral features.

The present disclosure provides systems and methods for intraoral imaging to enhance remote dental monitoring capabilities. As used herein, intraoral imaging may refer to the acquisition of one or more intraoral images and/or intraoral videos. The systems and methods disclosed herein may provide a convenient solution and user experience for dental patients to capture one or more intraoral images using a mobile device such as a smartphone. The systems and methods disclosed herein may allow patients to achieve a wide enough occlusion view for improved self-scans of a full dental arch, and may be more appealing to patients than a conventional cheek retractor system. The systems and methods disclosed herein may enhance a patient's ability to assess or evaluate their dental condition based on one or more full arch self-scans, and may provide dentists and orthodontists with a detailed analysis of the patient's dental condition based on one or more full arch scans captured remotely by the patient.

In an aspect, the present disclosure provides an intraoral adapter. The intraoral adapter may comprise an elongated housing comprising a viewing channel between a proximal portion and a distal portion of the elongated housing. In some embodiments, the viewing channel may be configured to define a field of view of an intraoral region of a subject's mouth for image capture using the camera of the mobile device.

In some embodiments, the elongated housing may comprise a flange that is sized and shaped to couple the intraoral adapter to the subject's mouth. In some embodiments, the flange may extend peripherally around an opening at the proximal portion of the elongated housing and may be configured to be positioned outside the field of view of the intraoral region of the subject's mouth.

In some embodiments, the intraoral adapter may comprise a mounting mechanism provided on the distal portion of the elongated housing. In some embodiments, the mounting mechanism may be configured to couple the intraoral adapter to a mobile device comprising a camera. In some embodiments, the mounting mechanism may be configured to couple the mobile device to the intraoral adapter such that a longitudinal axis of the viewing channel may be substantially aligned with an optical axis of the camera of the mobile device. In some embodiments, the mounting mechanism may be configured to mechanically engage with the mobile device or a casing of the mobile device. In some embodiments, the mounting mechanism may comprise an elastic band, a clamp, a hook, a magnet, a bracket, or a holder.

In some embodiments, the flange may extend continuously around a peripheral portion or perimeter of the opening. In some embodiments, the flange may extend outwards from the peripheral portion or the perimeter of the opening. In some embodiments, the flange may be configured to be inserted into the intraoral region of the subject's mouth such that the flange may be located between a lip portion and a gum portion of the subject's mouth. In some embodiments, the flange may comprise a concave curvature that is configured to conform to a shape or a structure of a gum portion of the subject's mouth.

In some embodiments, a cross-section of the viewing channel may be in a circular or elliptical shape. In some embodiments, a cross-section of the viewing channel may be in a shape that comprises at least three or more sides. In some embodiments, the cross-section of the viewing channel may be in a hexagonal shape. In some embodiments, the cross-section of the viewing channel may be in a regular shape that comprises two or more sides with a same length. In some embodiments, the cross-section of the viewing channel may be in an irregular shape that comprises two or more sides with different lengths.

In some embodiments, the flange may have a circular or elliptical shape. In some embodiments, the flange may have a shape that comprises at least three or more sides. In some embodiments, the flange may have a hexagonal shape. In some embodiments, the flange may have a regular shape that comprises two or more sides with a same length. In some embodiments, the flange may have an irregular shape that comprises two or more sides with different lengths.

In some embodiments, the field of view may have a circular or elliptical shape. In some embodiments, the field of view may have a shape that comprises at least three or more sides. In some embodiments, the field of view may have a hexagonal shape. In some embodiments, the field of view may have a regular shape that comprises two or more sides with a same length. In some embodiments, the field of view may have an irregular shape that comprises two or more sides with different lengths. In some embodiments, the field of view may be sized and shaped to improve capture of one or more intraoral images or intraoral videos of one or more molar regions of the subject's mouth.

In some embodiments, a length of the elongated housing or the viewing channel may be from about 20 millimeters (mm) to about 100 mm. In some embodiments, a cross-sectional width of the viewing channel may be from about 20 millimeters (mm) to about 100 mm. In some embodiments, a cross-sectional height of the viewing channel may be from about 10 millimeters (mm) to about 70 mm.

In some embodiments, the elongated housing may comprise an adjustable mechanism that may permit an orientation between the proximal portion and the distal portion of the elongated housing to be adjusted. In some embodiments, the orientation may comprise an angular displacement or a spatial displacement between the proximal portion and the distal portion of the elongated housing. In some embodiments, the angular displacement may range from about zero degrees to about 90 degrees.

In some embodiments, the elongated housing may comprise a first sub-housing comprising the proximal portion and a second sub-housing comprising the distal portion. In some embodiments, the first sub-housing and the second sub-housing may be operably coupled to each other via the adjustable mechanism. In some embodiments, the adjustable mechanism may comprise a rotatable mechanism that is configured to permit an adjustment of an orientation between the first sub-housing and the second sub-housing. In some embodiments, the rotatable mechanism may comprise a hinge, a knob, a dial, a gear, or a lever.

In some embodiments, the intraoral adapter may further comprise a mirror that is configured to adjust an optical path of the camera to enable the camera to capture one or more intraoral images of at least one of an upper dental arch and a lower dental arch of the subject.

In some embodiments, the intraoral adapter may further comprise an insertable mirror that is coupled to the elongated housing. In some embodiments, the insertable mirror may be configured to adjust an optical path of the camera to enable the camera to capture one or more intraoral images of at least one of an upper dental arch and a lower dental arch of the subject.

In some embodiments, the intraoral adapter may further comprise a sliding mechanism and a mirror that is coupled to the sliding mechanism. In some embodiments, the sliding mechanism may be configured to engage with a portion of the elongated housing and adjust a position or an orientation of the mirror relative to one or more intraoral regions of the subject's mouth. In some embodiments, the mirror may be configured to adjust an optical path of the camera to enable the camera to capture one or more intraoral images of at least one of an upper dental arch and a lower dental arch of the subject.

In some embodiments, one or more internal surfaces of the elongated housing may comprise a reflective surface that is configured to adjust an optical path of the camera to enable the camera to capture one or more intraoral images of at least one of an upper dental arch and a lower dental arch of the subject. In some embodiments, the reflective surface may comprise a mirror.

In another aspect, the present disclosure provides an intraoral imaging system. The intraoral imaging system may comprise an intraoral adapter. In some embodiments, the intraoral adapter may be operably coupled to a mobile device. In some embodiments, the intraoral imaging system may comprise an image processing unit configured to (i) process a plurality of intraoral images captured using the camera of the mobile device, and (ii) determine a dental condition of the subject based at least in part on the plurality of intraoral images.

In some embodiments, the image processing unit may be located onboard the mobile device. In some embodiments, the image processing unit may be located on one or more servers that are remote from the mobile device.

In some embodiments, the plurality of intraoral images may be captured using the camera of the mobile device. In some embodiments, the mobile device may be coupled to the intraoral adapter via the mounting mechanism.

In some embodiments, the dental condition may comprise (i) a movement of one or more teeth of the subject, (ii) an accumulation of plaque on the one or more teeth of the subject, (iii) a change in a color or a structure of the one or more teeth of the subject, (iv) a change in a color or a structure of a tissue adjacent to the one or more teeth of the subject, and/or (v) a presence or lack of presence of one or more cavities.

In some embodiments, the plurality of intraoral images may be usable to (i) predict a movement of one or more teeth of the subject, (ii) identify enamel wear patterns, (iii) create or modify a dental treatment plan, or (iv) generate or update an electronic medical record associated with the dental condition of the subject.

In some embodiments, the image processing unit may be configured to (i) generate a three-dimensional (3D) model of a dental structure of the subject based at least in part on the plurality of intraoral images, and (ii) determine a dental condition of the subject based at least in part on the three-dimensional model.

In some embodiments, the image processing unit may be configured to generate the 3D model based at least in part on an initial clinical scan of one or more intraoral regions of interest in the subject's mouth. In some embodiments, the initial clinical scan may comprise an initial three-dimensional (3D) model of the subject's dental structure that is generated before the plurality of intraoral images are captured using the camera of the mobile device.

In some embodiments, the three-dimensional (3D) model of the subject's dental structure may be generated based at least in part on motion data associated with a movement of the intraoral adapter relative to one or more intraoral regions of interest.

In some embodiments, the plurality of intraoral images may be usable to generate or update a dental treatment plan. In some embodiments, the plurality of intraoral images may be usable to track one or more changes in a dental structure or a dental condition of the subject over time. In some embodiments, the plurality of intraoral images may be usable to assess the subject's actual progress in relation to a dental treatment plan based at least in part on a comparison of (i) the one or more changes in the dental structure or the dental condition of the subject and (ii) a planned or estimated change in the dental structure or the dental condition of the subject.

In another aspect, the present disclosure provides a method for intraoral imaging. The method for intraoral imaging may comprise (a) providing an intraoral adapter; (b) using the mounting mechanism to couple the distal portion of the elongated housing of the intraoral adapter to the mobile device; (c) using the flange to couple the proximal portion of the elongated housing of the intraoral adapter to the subject's mouth; and (d) using the camera of the mobile device to image the intraoral region of the subject's mouth through the viewing channel of the intraoral adapter.

Another aspect of the present disclosure provides a non-transitory computer readable medium comprising machine executable code that, upon execution by one or more computer processors, implements any of the methods above or elsewhere herein.

Another aspect of the present disclosure provides a system comprising one or more computer processors and computer memory coupled thereto. The computer memory comprises machine executable code that, upon execution by the one or more computer processors, implements any of the methods above or elsewhere herein.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

DETAILED DESCRIPTION

Figure 1:
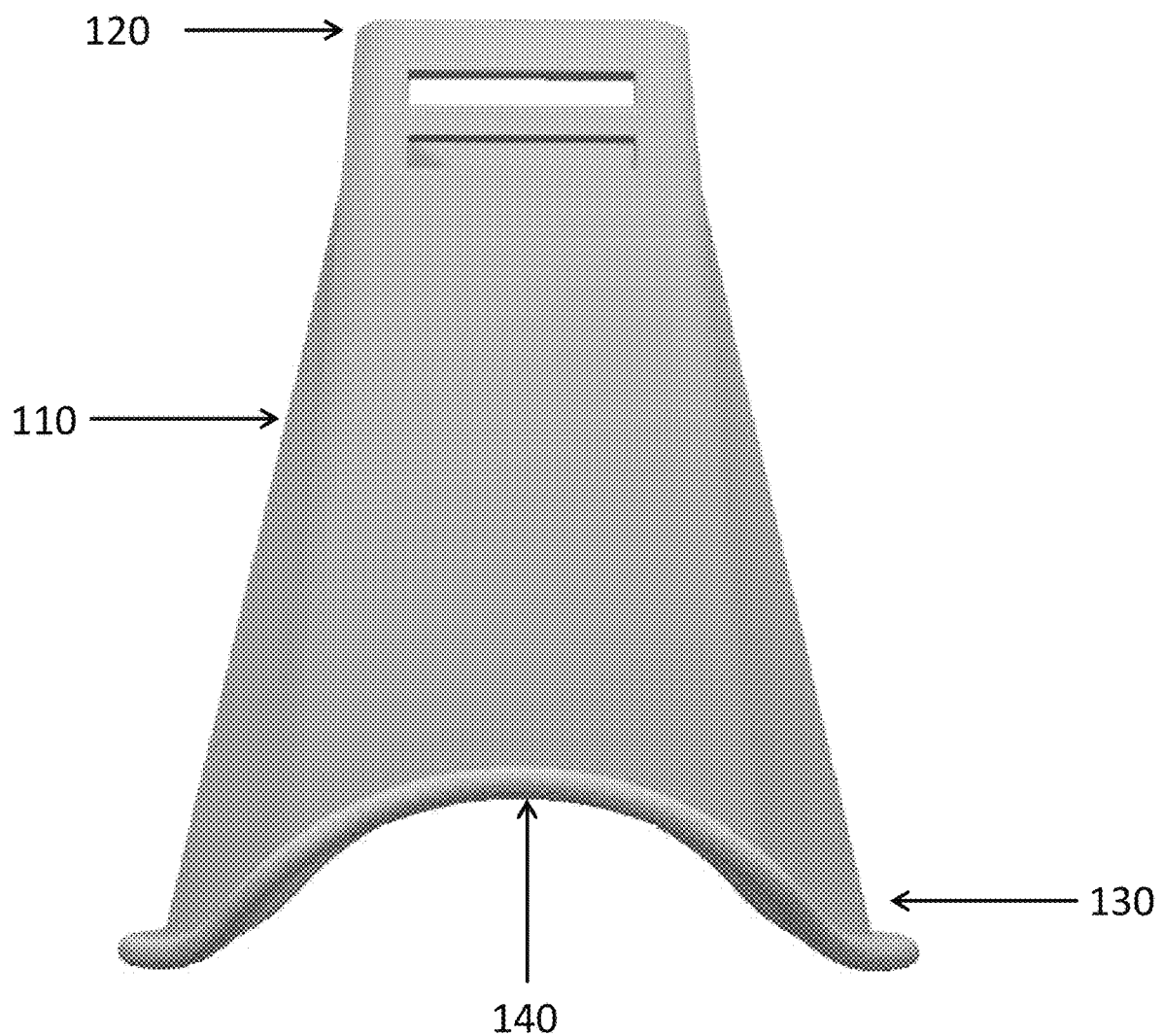
FIG. 1, FIG. 2, FIG. 3, FIG. 4, FIG. 5A, FIG. 5B, FIG. 6A, FIG. 6B, and FIG. 6C schematically illustrate various examples of an intraoral adapter from different perspectives, in accordance with some embodiments.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The term "real-time," as used herein, generally refers to a simultaneous or substantially simultaneous occurrence of a first event or action with respect to an occurrence of a second event or action. A real-time action or event may be performed within a response time of less than one or more of the following: ten seconds, five seconds, one second, a tenth of a second, a hundredth of a second, a millisecond, or less relative to at least another event or action. A real-time action may be performed by one or more computer processors.

Whenever the term "at least," "greater than," or "greater than or equal to" precedes the first numerical value in a series of two or more numerical values, the term "at least," "greater than" or "greater than or equal to" applies to each of the numerical values in that series of numerical values. For example, greater than or equal to 1, 2, or 3 is equivalent to greater than or equal to 1, greater than or equal to 2, or greater than or equal to 3.

Whenever the term "no more than," "less than," or "less than or equal to" precedes the first numerical value in a series of two or more numerical values, the term "no more than," "less than," or "less than or equal to" applies to each of the numerical values in that series of numerical values. For example, less than or equal to 3, 2, or 1 is equivalent to less than or equal to 3, less than or equal to 2, or less than or equal to 1.

The terms "a," "an," and "the," as used herein, generally refer to singular and plural references unless the context clearly dictates otherwise.

Overview

In an aspect, the present disclosure provides a system for remote dental monitoring. The system may comprise an intraoral adapter. The intraoral adapter may be used by a user or a subject (e.g., a dental patient) in conjunction with a mobile device to remotely monitor a dental anatomy or a dental condition of the subject. A dental anatomy may comprise one or more dental structures of the patient, including one or more tooth structures or dental arches of the subject. The dental condition may comprise a development, appearance, and/or condition of the subject's teeth. In some cases, the dental condition may comprise a functional aspect of the user's teeth, such as how two or more teeth contact each other.

As used herein, remote monitoring may refer to monitoring a dental anatomy or a dental condition of a patient that is performed at one or more locations remote from the patient. For example, a dentist or a medical specialist may monitor the dental anatomy or dental condition in a first location that is different than a second location where the patient is located. The first location and the second location may be separated by a distance spanning at least 1 meter, 1 kilometer, 10 kilometers, 100 kilometers, 1000 kilometers, or more. The remote monitoring may be performed by assessing a dental anatomy or a dental condition of the subject using one or more intraoral images captured by the subject when the patient is located remotely from the dentist or a dental office. In some cases, the remote monitoring may be performed in real-time such that a dentist is able to assess the dental anatomy or the dental condition when a subject uses a mobile device to acquire one or more intraoral images of one or more intraoral regions in the patient's mouth. The remote monitoring may be performed using equipment, hardware, and/or software that is not physically located at a dental office.

Intraoral Adapter

As described above, the remote dental monitoring systems disclosed herein may comprise an intraoral adapter. The intraoral adapter may comprise an elongated housing comprising a viewing channel between a proximal portion and a distal portion of the elongated housing. In some embodiments, the intraoral adapter may comprise a single, unitary structure. In other embodiments, the intraoral adapter may comprise a plurality of components that can be coupled, attached, or integrated together to form the intraoral adapter.

FIG. 1, FIG. 2, FIG. 3, FIG. 4, FIG. 5A, FIG. 5B, FIG. 6A, FIG. 6B, and FIG. 6C illustrate an elongated housing 110 of the intraoral adapter from different perspectives. The elongated housing may comprise a distal end 120 and a proximal end 130. A mobile device may be placed at, on, near, or adjacent to the distal end 120 in order to capture one or more intraoral images of one or more intraoral regions in a subject's mouth. The mobile device may comprise one or more imaging devices (e.g., one or more cameras) that can be configured to capture the one or more intraoral images. The proximal end 130 may comprise a flange 140. The flange 140 may be placed in a subject's mouth between a tooth portion and a gum portion of the subject's mouth.

The elongated housing 110 may comprise a viewing channel 150. The viewing channel 150 may comprise an elongated hollow region that extends from the distal end 120 to the proximal end 130 of the elongated housing 110. The viewing channel can be configured to permit one or more cameras of a mobile device to capture one or more intraoral images or intraoral videos through a length of the intraoral adapter.

Figure 2:
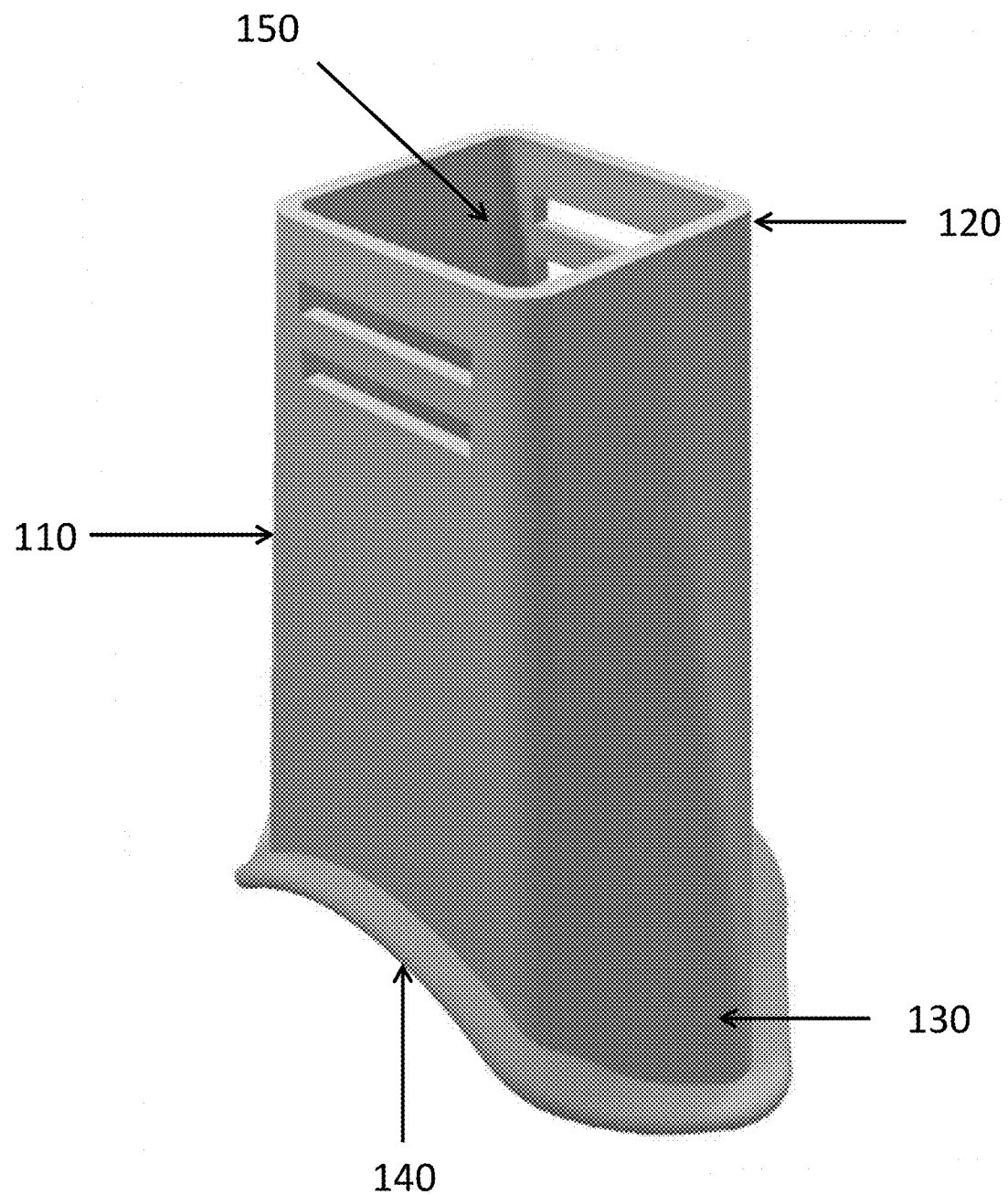
Figure 3:
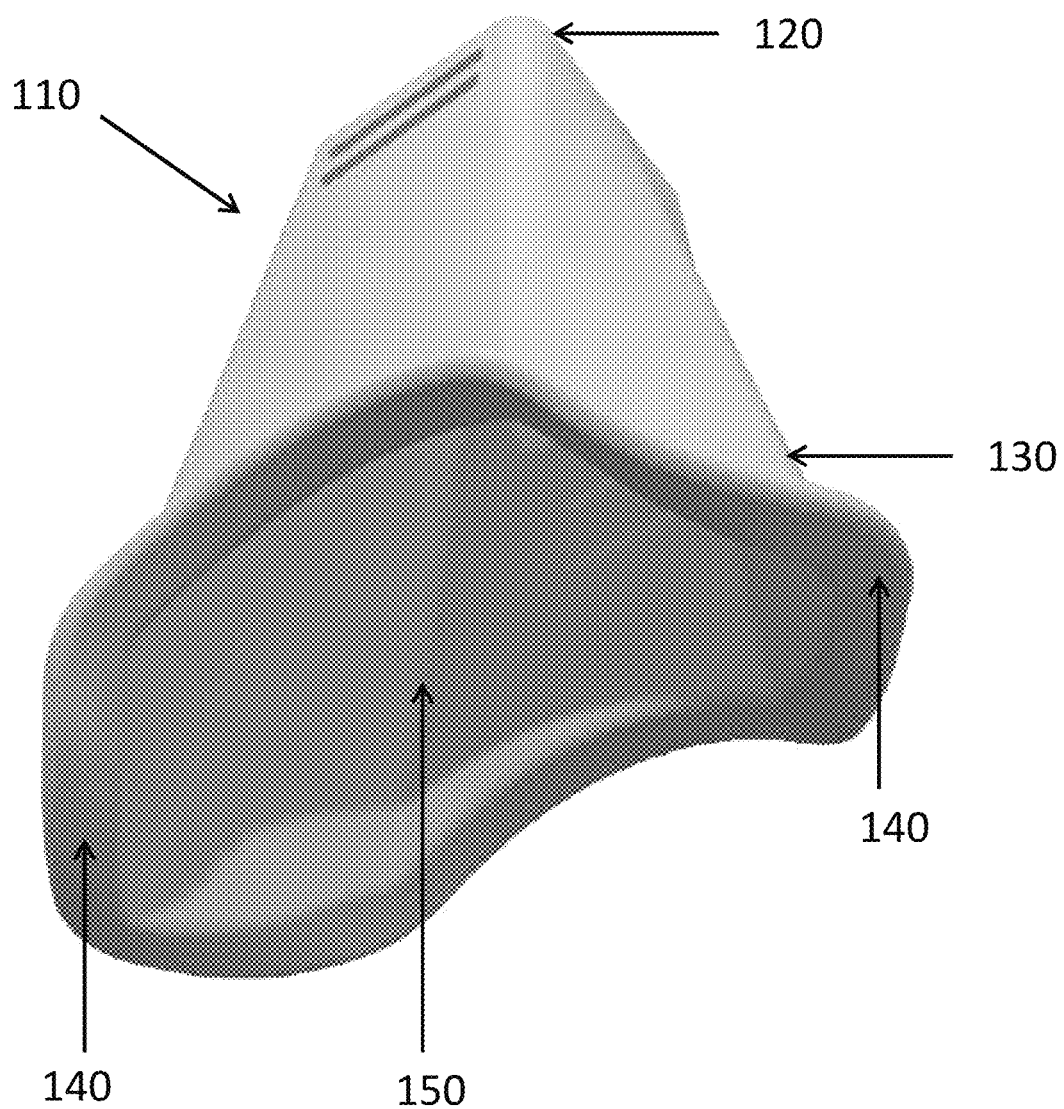

As shown in FIG. 2 and FIG. 3, the distal end 120 and the proximal end 130 may comprise different cross-sectional shapes. For example, the distal end 120 may comprise a first cross-sectional shape and the proximal end 130 may comprise a second cross-sectional shape that is different than the first cross-sectional shape. The first cross-sectional shape and/or the second cross-sectional shape may comprise a circle, a triangle, a square, a rectangle, a pentagon, a hexagon, or any shape having three or more sides. A cross-section of the distal end 120 may be circular, triangular, square, rectangular, pentagonal, hexagonal, an n-sided shape having at least three or more sides, or any partial cross-section or combination of cross-sections thereof. A cross-section of the proximal end 130 may be circular, triangular, square, rectangular, pentagonal, hexagonal, an n-sided shape having at least three or more sides, or any partial cross-section or combination of cross-sections thereof. The n-sided shape may comprise two or more sides that are of a same length. The n-sided shape may comprise two or more sides with different lengths. In some cases, the first cross-sectional shape and the second cross-sectional shape may comprise a similar shape with different dimensions.

Figure 4:
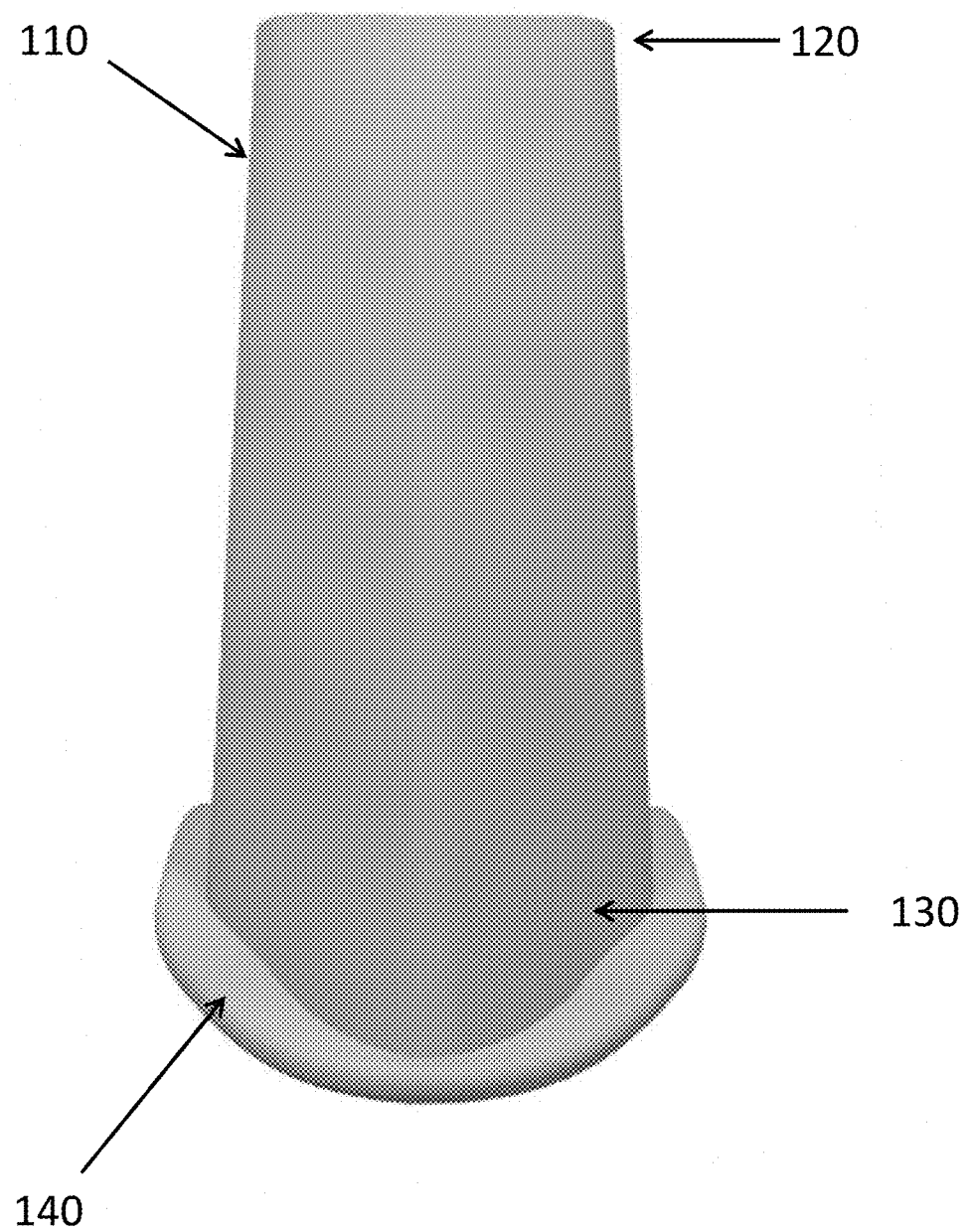

In some cases, a cross-sectional width of the distal end 120 of the elongated housing 110 may be different than a cross-sectional width of the proximal end 130 of the elongated housing 110. For example, a cross-sectional width of the distal end 120 of the elongated housing 110 may be less than a cross-sectional width of the proximal end 130 of the elongated housing 110. In such cases, a cross-sectional width of the elongated housing 110 may gradually increase along a length of the elongated housing 110 between the distal end 120 and the proximal end 130 of the elongated housing 110. As shown in FIG. 1 and FIG. 4, the cross-sectional width of the elongated housing 110 may gradually increase from the distal end 120 of the elongated housing 110 to the proximal end 130 of the elongated housing 110. In some cases, a cross-sectional width of the distal end 120 of the elongated housing 110 may be greater than a cross-sectional width of the proximal end 130 of the elongated housing 110. In such cases, a cross-sectional width of the elongated housing 110 may gradually decrease along a length of the elongated housing 110 between the distal end 120 and the proximal end 130 of the elongated housing 110.

Figure 5A:
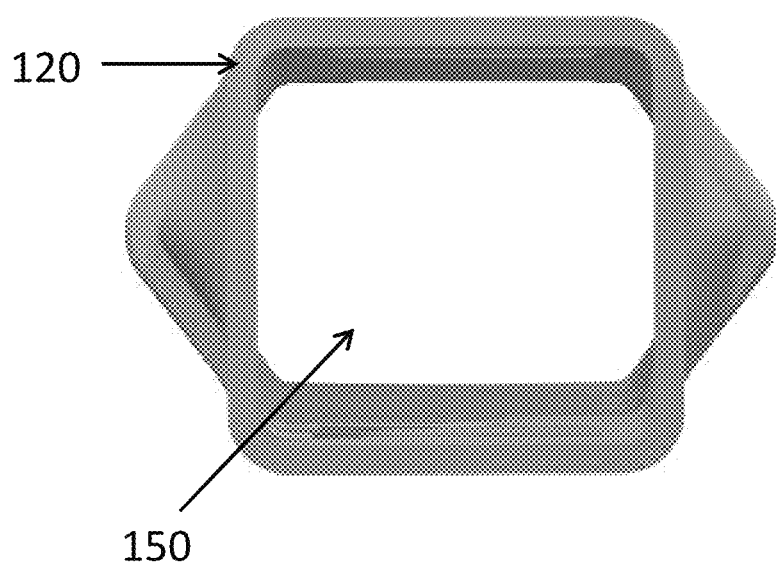
Figure 5B:
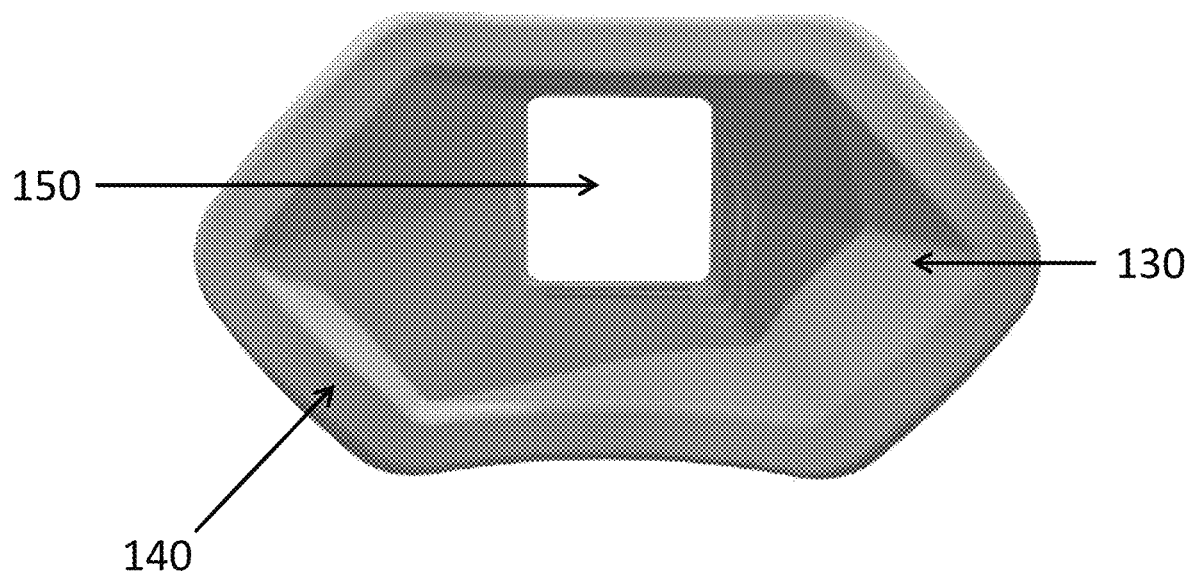

As shown in FIG. 5A and FIG. 5B, a dimension of the viewing channel 150 may also vary in size and/or shape between the distal end 120 of the elongated housing 110 and the proximal end 130 of the elongated housing 110. The cross-sectional width of the viewing channel 150 may gradually increase from the distal end 120 of the elongated housing 110 to the proximal end 130 of the elongated housing 110. Further, a cross-sectional shape of the viewing channel 150 at the distal end 120 of the elongated housing 110 may be different than a cross-sectional shape of the viewing channel 150 at the proximal end 130 of the elongated housing 110.

The viewing channel 150 of the elongated housing 110 may be configured to define a field of view of an intraoral region of a subject's mouth. The field of view may be sized and/or shaped to permit one or more cameras of the mobile device to capture one or more images of one or more intraoral regions in a subject's mouth. In some cases, the one or more images may comprise one or more intraoral images showing a portion of a subject's mouth. In some cases, the one or more images may comprise one or more intraoral images showing a full dental arch of the subject.

The field of view may have a width that is at least about 1 inch, 2 inches, 3 inches, 4 inches, 5 inches, or more. The field of view may have a height that is at least about 1 inch, 2 inches, 3 inches, 4 inches, 5 inches, or more. The dimensions of the field of view may be adjusted or may vary depending on the anatomical characteristics of the subject or patient.

Figure 6A:
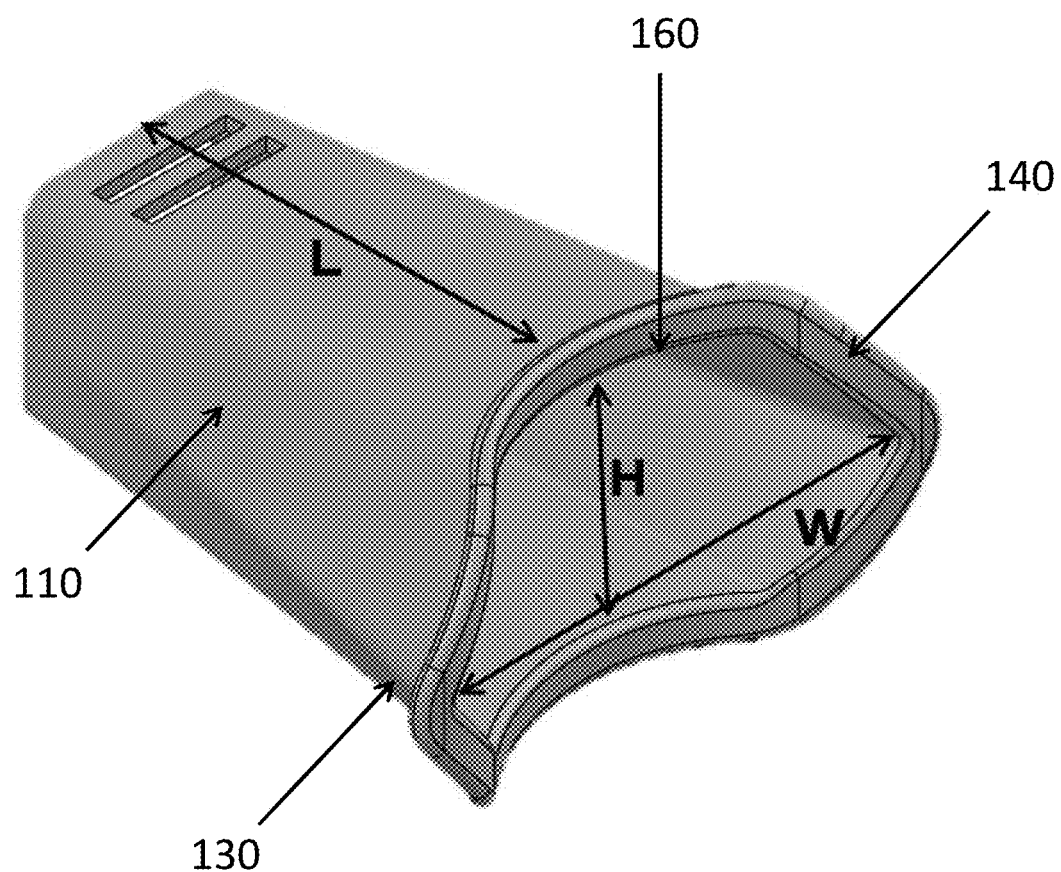
Figure 6B:
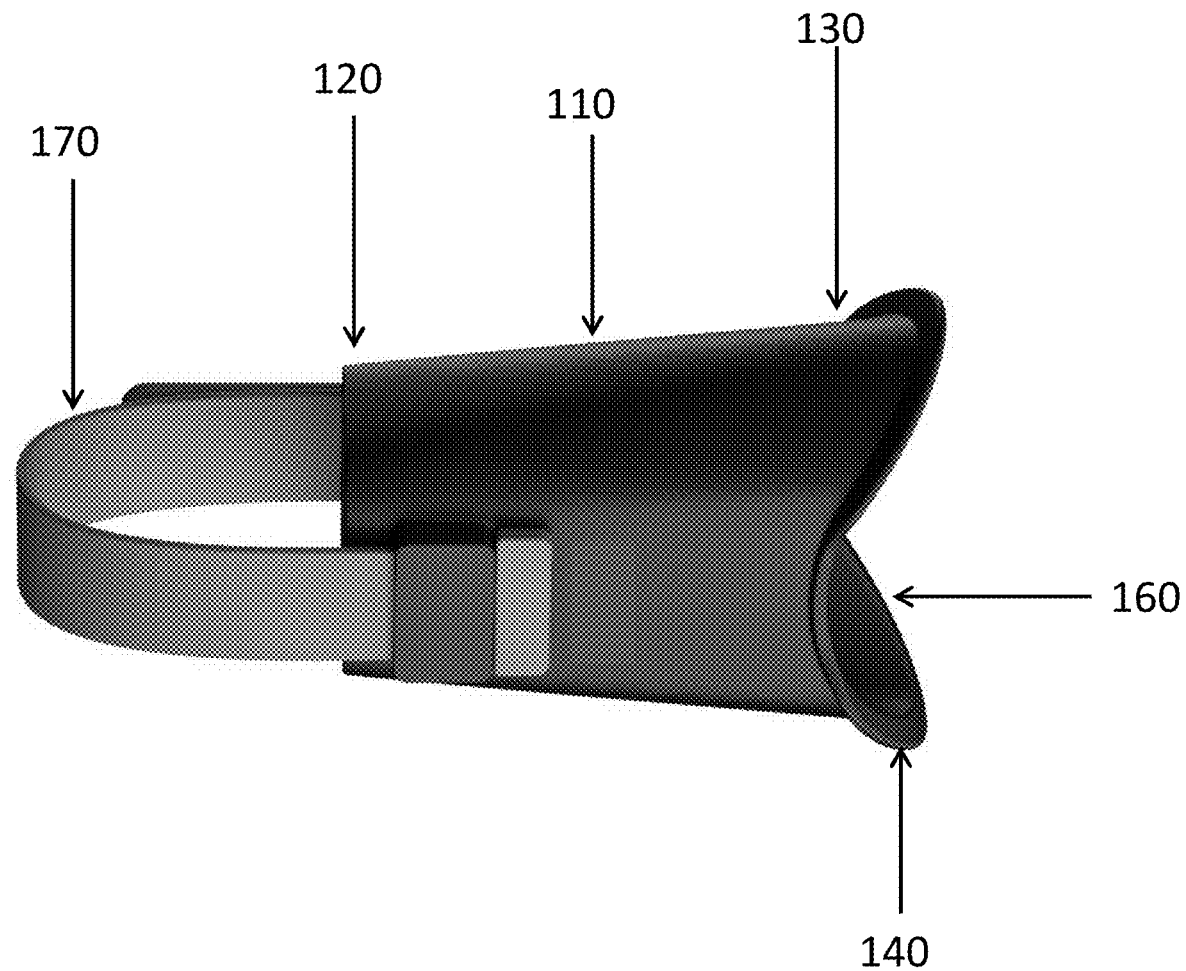
Figure 6C:
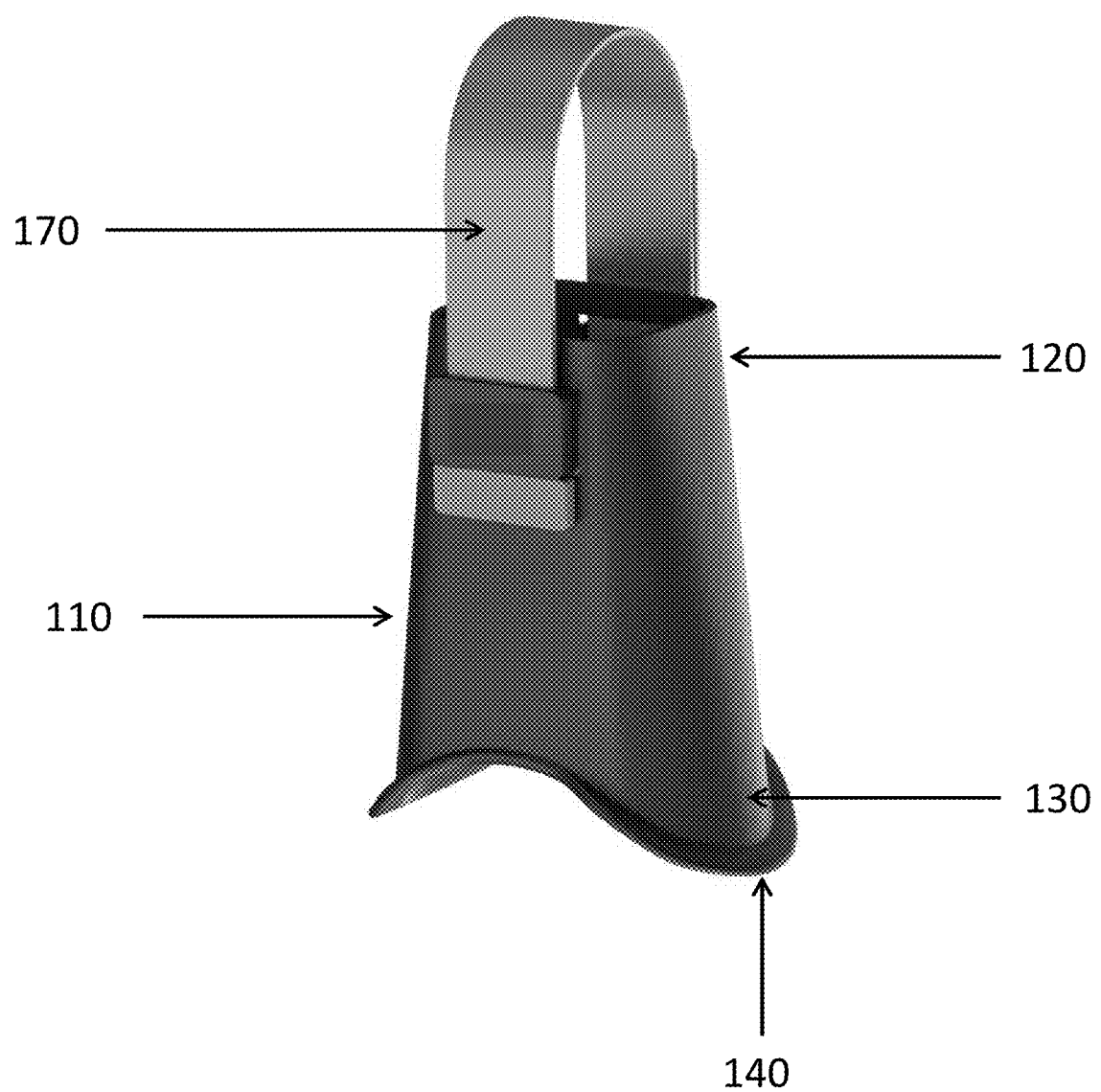

As shown in FIG. 6A, FIG. 6B, and FIG. 6C, the elongated housing 110 of the intraoral adapter may comprise a flange 140. In some cases, the flange 140 may be integrated with the elongated housing 110 to form a single unitary piece. In other cases, the flange 140 may not or need not be integrated with the elongated housing 110, and may be provided as a separate component that can be releasably attached or coupled to the intraoral adapter. The flange 140 may extend peripherally around an opening 160 at the proximal portion 130 of the elongated housing. In some cases, the flange 140 may extend peripherally around a section or a portion of the opening 160. The flange 140 may be sized and shaped to couple the intraoral adapter to the subject's mouth when the flange 140 is positioned between a gum portion and a tooth portion of the subject's mouth. The flange may be configured to be inserted into an intraoral region of the subject's mouth such that the flange is located between a lip portion and a gum portion of the subject's mouth. The intraoral adapter may be suspended from the subject's mouth when the flange 140 is positioned between the gum portion and the tooth portion of the subject's mouth. The gum portion and the tooth portion may be in contact with a first side of the flange 140 and a second side of the flange 140 to support a weight of the intraoral adapter when the intraoral adapter is suspended from the subject's mouth. The flange 140 may be sized and shaped to permit the subject to move the intraoral adapter and/or to adjust a position or an orientation of the intraoral adapter relative to one or more intraoral regions in the subject's mouth. Adjusting the position or the orientation of the intraoral adapter relative to one or more intraoral regions in the subject's mouth may also adjust a position or an orientation of the camera of the mobile device relative to the one or more intraoral regions in the subject's mouth. Adjusting a position or an orientation of the camera of the mobile device relative to the one or more intraoral regions in the subject's mouth may further adjust a relative position and/or a relative orientation of an optical axis of the camera relative to the one or more intraoral regions in the subject's mouth. The flange 140 may remain between the gum portion and the tooth portion of the subject's mouth while the subject moves the intraoral adapter around in the subject's mouth. The flange 140 may be sized and shaped to permit the subject to capture one or more intraoral images of a full dental arch of the subject (or a portion thereof).

In any of the embodiments described herein, the flange 140 of the intraoral adapter may be configured to be positioned outside the field of view defined by the viewing channel of the intraoral adapter. As described above, the field of view may be configured to provide a view of an intraoral region of the subject's mouth. The flange 140 may be configured to extend radially outwards from a perimeter of the opening 160 such that the flange 140 is positioned outside the field of view 180 of the intraoral region of the subject's mouth. The flange may extend partially or continuously around a peripheral portion or perimeter of the opening. The flange may extend outwards from the peripheral portion or the perimeter of the opening.

In some cases, the flange may comprise a concave curvature that is configured to conform to a shape or a structure of a gum portion of the subject's mouth. The concave curvature may comprise one or more curved portions configured to conform to a curvature of one or more portions of the subject's gums. The one or more curved portions may have a radius of curvature ranging from about 0.1 inches to about 10 inches. In some embodiments, the radius of curvature may be less than or equal to about 0.1 inches. In other embodiments, the radius of curvature may be greater than or equal to about 10 inches.

The flange may be configured to extend from the body of the intraoral adapter at an angle. The angle may be at least about 5 degrees, 10 degrees, 15 degrees, 20 degrees, 25 degrees, 30 degrees, 35 degrees, 40 degrees, 45 degrees, 50 degrees, 60 degrees, 70 degrees, 80 degrees, 90 degrees, 100 degrees, 110 degrees, 120 degrees, or more.

In some cases, the flange may have a thickness that ranges from about 1 millimeter to about 10 millimeters. In some cases, the flange may have a thickness that is greater than about 10 millimeters. In some cases, the flange may extend outwards from a body of the intraoral adapter by at least about 1 millimeter to about 10 millimeters. In some cases, the flange may extend outwards from a body of the intraoral adapter by more than about 10 millimeters.

Figure 6D:
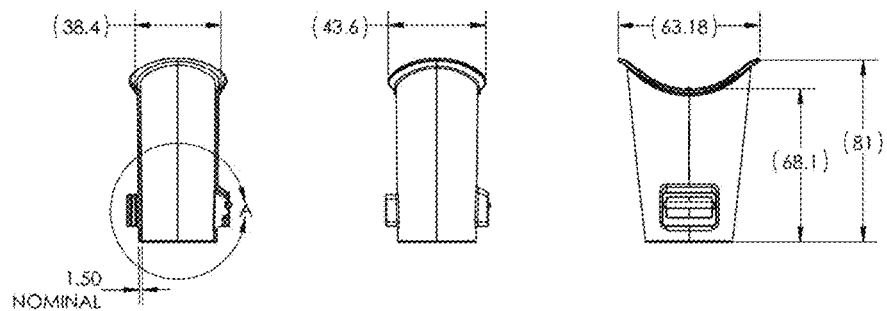
FIG. 6D, FIG. 6E, and FIG. 6F schematically illustrate various examples of an intraoral adapter with one or more reduced dimensions, in accordance with some embodiments.
Figure 6E:
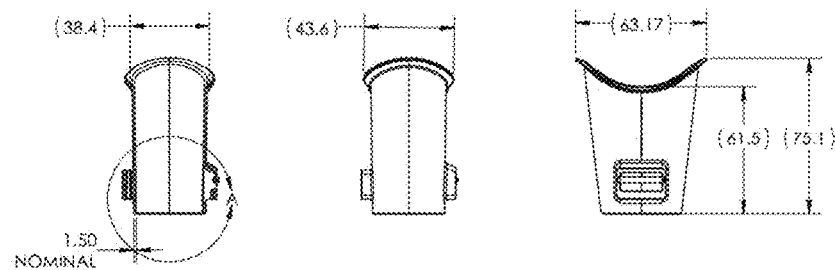
Figure 6F:
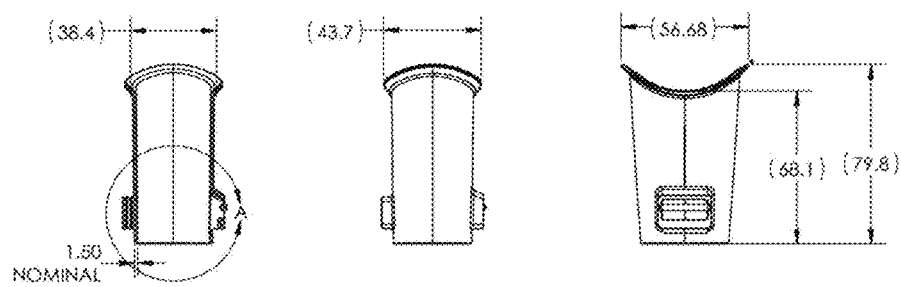
Figure 7A:
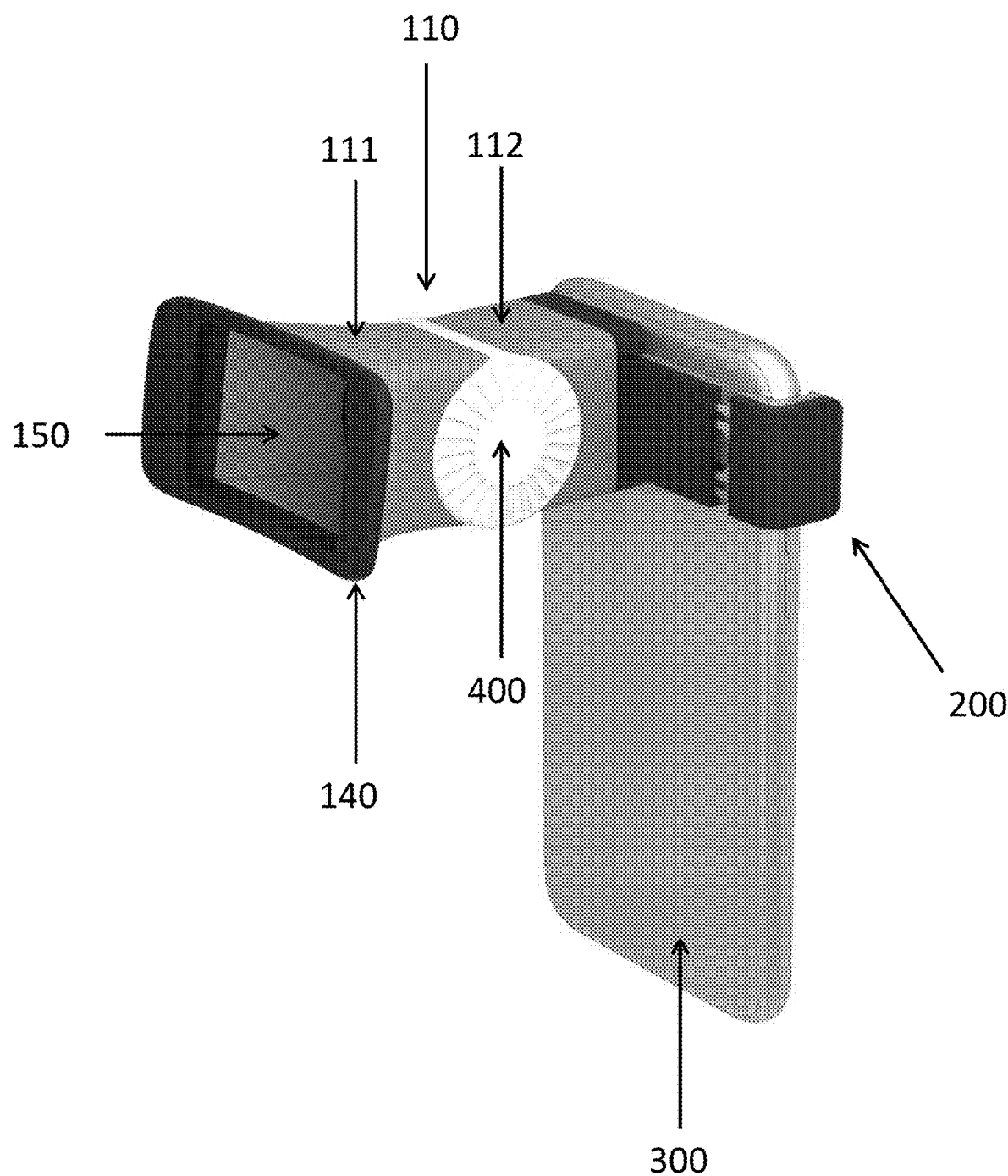
FIG. 7A, FIG. 7B, FIG. 7C, FIG. 7D, FIG. 8, and FIG. 9 schematically illustrate a mobile device coupled to the intraoral adapter via a mounting mechanism from different perspectives, in accordance with some embodiments.
Figure 7B:
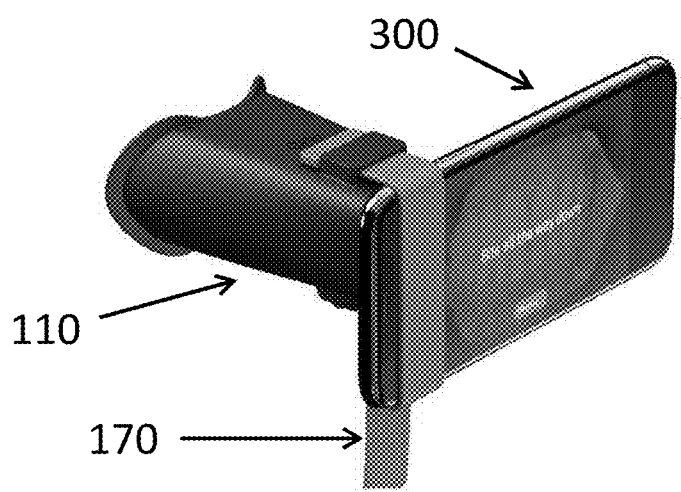
Figure 7C:
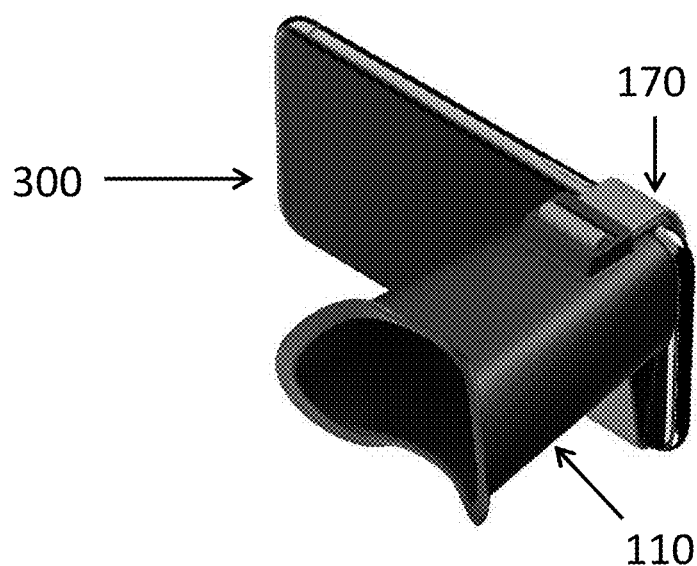
Figure 7D:
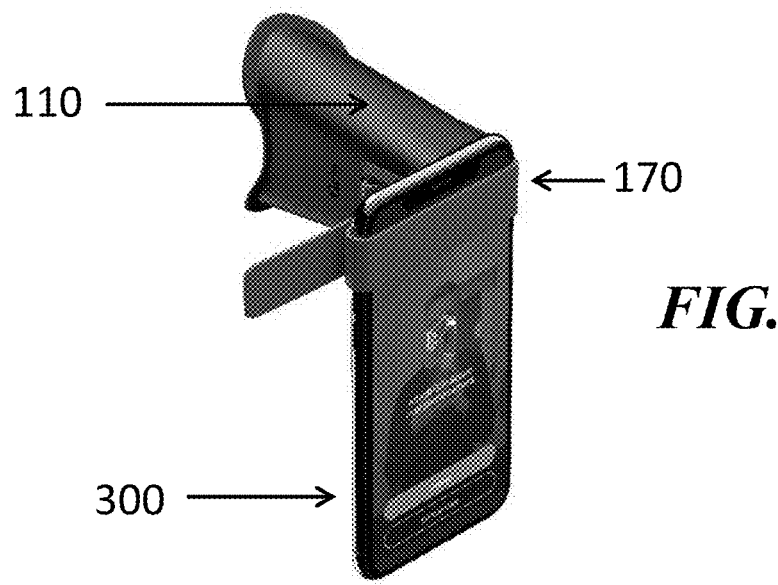
Figure 8:
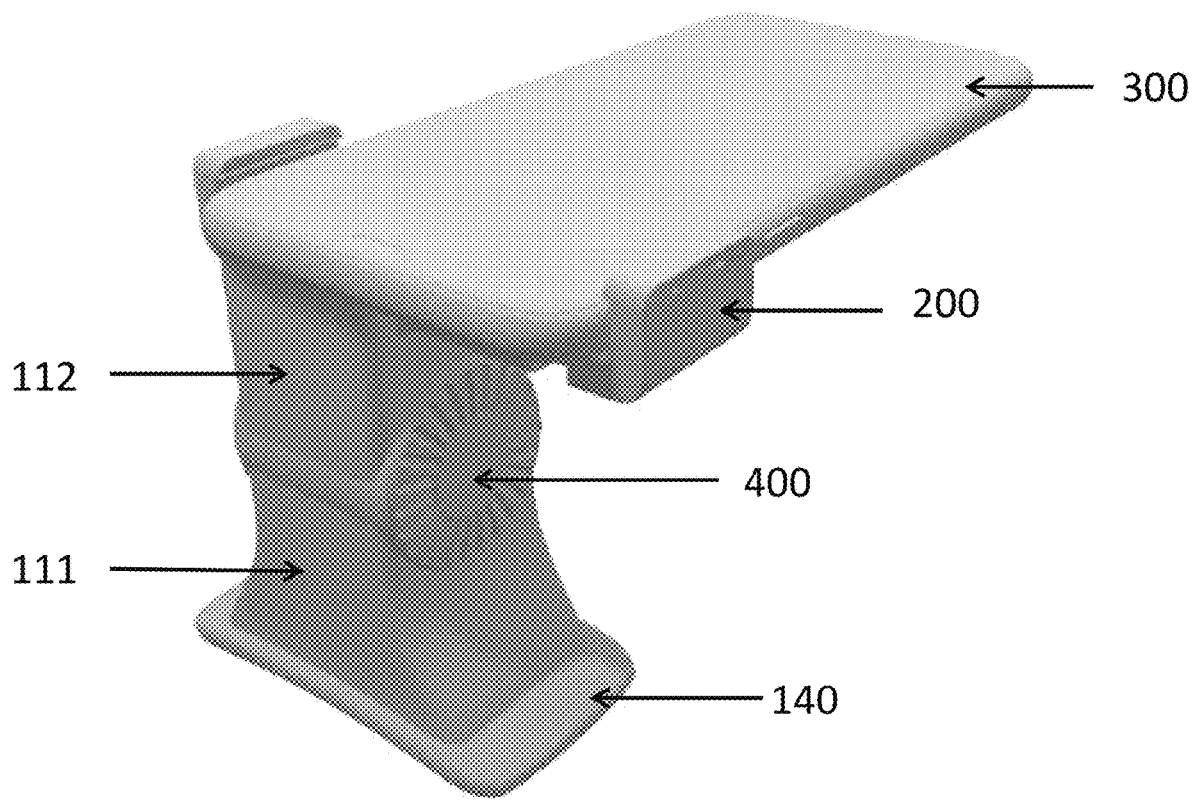

FIG. 6D, FIG. 6E, and FIG. 6F schematically illustrate various examples of an intraoral adapter with one or more reduced dimensions. The intraoral adapters illustrated in FIG. 6D, FIG. 6E, and FIG. 6F may be sized and/or shaped for use by younger patients (e.g., children), and may comprise the same features and functionalities as the intraoral adapters described and referred to elsewhere herein. In one example, as shown in FIG. 6D, the intraoral scope may have a 15% reduction in opening size to accommodate younger patients. The reduced opening size of the intraoral adapter may range from about 60 millimeters to about 65 millimeters. In another example, as shown in FIG. 6E, the intraoral scope may have a 15% reduction in opening size and a 10% reduction in height to accommodate younger patients. The reduced opening size of the intraoral adapter may range from about 60 millimeters to about 65 millimeters, and the reduced height of the intraoral adapter may range from about 70 millimeters to about 80 millimeters. In yet another example, as shown in FIG. 6F, the intraoral scope may have a 25% reduction in opening size to accommodate younger patients. The reduced opening size of the intraoral adapter may range from about 50 millimeters to about 60 millimeters.

The flange may comprise a first material. The first material may comprise a soft, compliant material. The first material may comprise a rubber material, a silicone material, a polymeric material, a thermoplastic elastomer, and/or a synthetic rubber material such as styrene-butadiene rubber, ethylene propylene diene monomer rubber, isoprene, chloroprene, polychloroprene, neoprene, or isobutylene. The intraoral adapter may comprise a second material. The second material may comprise a plastic material. The plastic material may comprise polyethylene terephthalate (PETE or PET), high-density polyethylene (HDPE), polyvinyl chloride (PVC), low-density polyethylene (LDPE), polypropylene (PP), polycarbonate, polylactide, acrylic, acrylonitrile butadiene, styrene, fiberglass, nylon, and/or any combination thereof. In some cases, the second material may comprise a metallic material. The metallic material may comprise steels such as carbon steels and/or stainless steels, pure metals such as copper and/or aluminum, or metal alloys such as bronze and/or brass. In some cases, the second material may comprise a combination of plastic materials and metallic materials. In some cases, the second material may be different than the first material. In other cases, the second material may be the same as the first material.

In some cases, the first material and/or the second material may comprise polyvinyl chloride, polyvinylidene chloride, low density polyethylene, linear low density polyethylene, polyisobutene, poly[ethylene-vinylacetate] copolymer, and/or thermoplastics such as polyaryletherketone (PAEK), polyetheretherketone (PEEK), polyetherketoneketone (PEKK), polyetherketone (PEK), carbon-PEEK composites, PEEK-BaSO4 polymeric rubbers, polyethylene terephthalate (PET), silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, and/or rigid polymers including polyphenylene, polyamide, polyimide, polyetherimide, polyethylene, or epoxy. In some cases, the first material and/or the second material may comprise acrylobutadiene styrene (ABS), polypropylene (PP), polystyrene (PS), polycarbonate (PC), polysulfone (PS), polyphenyl sulfone (PPSU), polymethyl methacrylate (acrylic) (PMMA), polyethylene (PE), ultra high molecular weight polyethylene (UHMWPE), lower density polyethylene (LPDE), polyamide (PA), liquid crystal polymer (LCP), polyaryl amide (PARA), polyphenyl sufide (PPS), polyether etherketone (PEEK), polyvinyl chloride (PVC), polyethylene terephthalate (PET), polytetra flouroethylene (PTFE), polyaryletherketone (PAEK), polyphenyl sulfone (PPSU), and/or a combination thereof.

In some cases, the flange and/or the intraoral adapter may comprise a material that is manufacturable using stereolithography. In such cases, the material may comprise one or more photosensitive resins or thermoset polymers. The one or more photosensitive resins or thermoset polymers may be selectively cured layer-by-layer when exposed to a light source. In some cases, the light source may comprise an ultraviolet (UV) light or laser beam.

In some cases, the flange and/or the intraoral adapter may comprise a biocompatible material. A biocompatible material may comprise a material that is compatible for use with biological materials. A biocompatible material may comprise a material that does not produce allergic reactions and/or toxic or injurious effects on the subject when placed in the subject's mouth. The biocompatible material may not elicit any undesirable local or systemic biological or physiological effects when placed in the subject's mouth. In some examples, the biocompatible material may comprise one or more polymeric materials including, but not limited to, thermosets, elastomers, and/or other polymeric materials that may be created by polymerizing monomers and/or cross-linking oligomers. In other examples, the biocompatible material may comprise materials such as cellophane, vinyl, acetate, polyethylene acrylic, butyl rubber, ethylene-vinyl acetate, natural rubber, a nitrile, silicone rubber, a styrene block copolymer, and/or a vinyl ether. Optionally, in any of the embodiments disclosed herein, the biocompatible material may comprise one or more antimicrobial and/or antiseptic materials, for example sodium bicarbonate; hydrogen peroxide; benzalkonium chloride; chlorhexidine; hexachlorophene; iodine compounds; and/or any combinations thereof.

FIG. 6B, FIG. 6C, FIG. 7B, FIG. 7C, and FIG. 7D schematically illustrate another embodiment of an intraoral adapter that may be used to capture one or more intraoral images or videos. In some embodiments, the intraoral adapter may comprise an attachment mechanism 170 for coupling a mobile device 300 to the intraoral adapter. The attachment mechanism 170 may comprise, for example, a strap for securing the mobile device 300 to the intraoral adapter. The strap may comprise a flexible and/or compliant material, such as silicone. In some cases, the strap may comprise any biocompatible material, or any material that is dishwasher safe. The strap may be adjustable to enable a user to couple various mobile devices having different sizes, shapes, and/or form factors to the intraoral adapter. The adjustability of the strap may provide several advantages, including improved compatibility with different mobile devices having distinct camera configurations, or imaging sensors disposed on different portions or locations on the mobile device.

Shapes

In some cases, a cross-section of the viewing channel may be in a circular or elliptical shape. In some cases, a cross-section of the viewing channel may be in a shape that comprises at least three or more sides. In some cases, the cross-section of the viewing channel may be in a hexagonal shape. In some cases, the cross-section of the viewing channel may be in a regular shape that comprises two or more sides with a same length. In other cases, the cross-section of the viewing channel may be in an irregular shape that comprises two or more sides with different lengths.

In some cases, the flange may have a circular or elliptical shape. In some cases, the flange may have a shape that comprises at least three or more sides. In some cases, the flange may have a hexagonal shape. In some cases, the flange may comprise a regular shape that comprises two or more sides with a same length. In some cases, the flange may comprise an irregular shape that comprises two or more sides with different lengths.

In some cases, the field of view may have a circular or elliptical shape. In some cases, the field of view may have a shape that comprises at least three or more sides. In some cases, the field of view may have a hexagonal shape. In some cases, the field of view may have a regular shape that comprises two or more sides with a same length. In some cases, the field of view may have an irregular shape that comprises two or more sides with different lengths. The field of view may be sized and shaped to improve capture of one or more intraoral images or intraoral videos of one or more molar regions of the subject's mouth. The field of view may be sized and/or shaped to reduce or minimize an amount of movement and/or adjustment needed by the subject to align an optical axis of the camera of the mobile device with the one or more molar regions.

In some cases, a cross-sectional shape of the viewing channel may comprise an irregular or amorphous shape. In some cases, a shape of the flange may comprise an irregular or amorphous shape. In some cases, a shape of the field of view may comprise an irregular or amorphous shape. An irregular shape may comprise a shape with a plurality of sides having one or more different lengths. An amorphous shape may comprise a shape that does not correspond to a circle, an ellipse, or a polygon.

Figure 10:
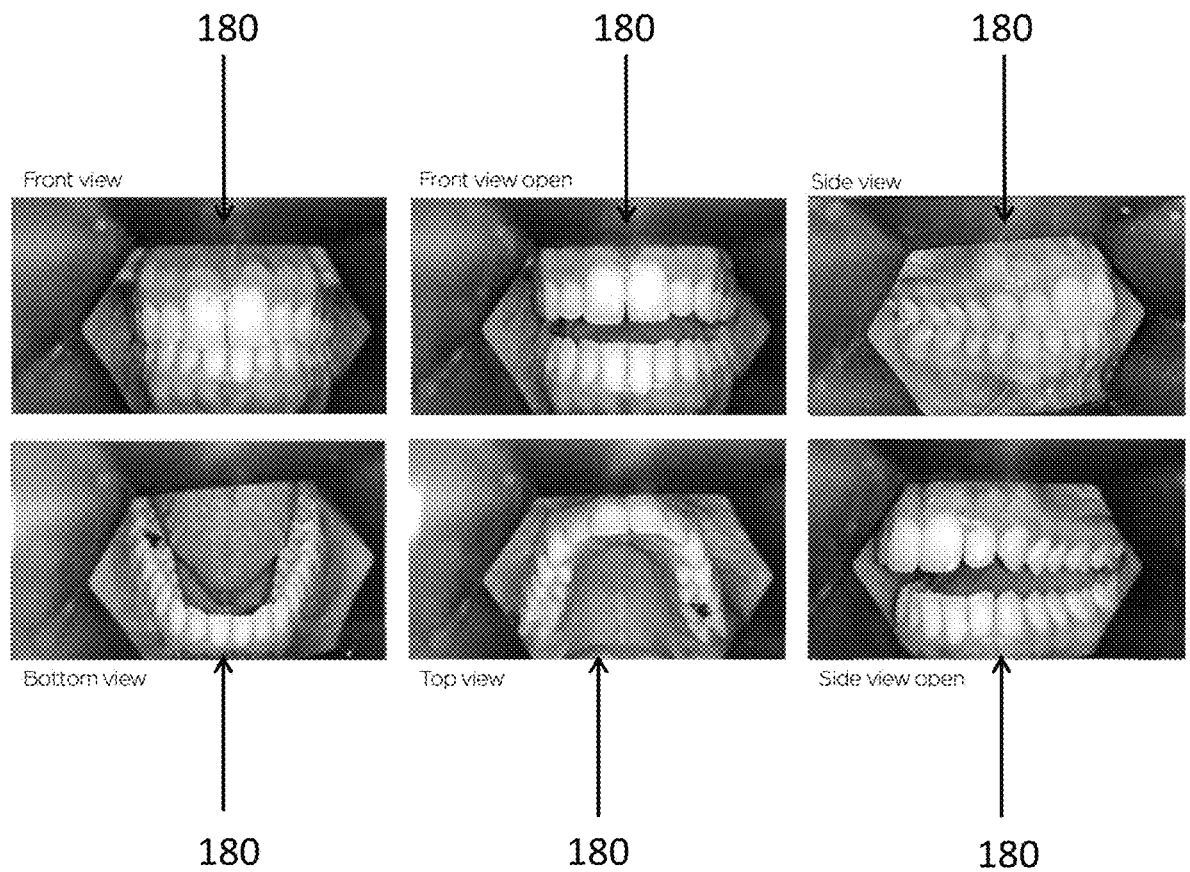
FIG. 10 schematically illustrates a field of view defined by a viewing channel of the elongated housing, in accordance with some embodiments.

FIG. 10 illustrates a field of view 180 defined by a viewing channel of any one or more intraoral adapters provided herein. The field of view 180 may be sized and shaped to provide the camera of the mobile device with a visualization of at least a portion of the subject's mouth. The field of view 180 may be sized and shaped to permit the camera of the mobile device to capture one or more intraoral images or videos comprising a front view, a side view, a bottom view, and/or a top view of one or more portions of the subject's upper dental arch or lower dental arch. The field of view 180 may be sized and shaped to permit the subject to capture one or more intraoral images or videos comprising a full dental arch of the subject. The field of view 180 may be sized and shaped to permit the camera of the mobile device to capture one or more intraoral images or videos while the subject is biting down (i.e., when the subject's upper dental arch and lower dental arch are in contact with or adjacent to each other). The field of view 180 may be sized and shaped to permit the camera of the mobile device to capture one or more intraoral images or videos while the subject is not biting down completely (i.e., when at least a portion of the subject's upper dental arch and lower dental arch are not in contact with each other, or when the subject's upper dental arch and lower dental arch are separated by a separation distance). In cases where the subject moves the intraoral adapter to image different intraoral regions within the subject's mouth, the field of view 180 may be sized and shaped to reduce or minimize an amount of movement or adjustment required by the subject to image one or more molar regions of the subject's mouth.

As shown in FIG. 10, the field of view 180 may comprise a hexagonal shape having six sides. In some cases, at least two of the six sides of the hexagonal shape may have a different length. In other cases, each of the six sides of the hexagonal shape may have a same length. In some cases, two or more internal angles of the hexagonal shape may be different. In other cases, each internal angle of the hexagonal shape may be the same.

Dimensions

In some cases, a length of the elongated housing or the viewing channel may range from about 20 millimeters (mm) to about 100 mm. In some cases, a cross-sectional width of the elongated housing or the viewing channel may range from about 20 millimeters (mm) to about 100 mm. In some cases, a cross-sectional height of the elongated housing or the viewing channel may range from about 10 millimeters (mm) to about 70 mm.

In some embodiments, the field of view provided by the intraoral adapter may have a width and a height associated with the field of view. In some cases, the width of the field of view may be greater than or equal to the height of the field of view. In such cases, the width of the field of view may permit imaging of the back molar regions of a subject from various perspectives while reducing or minimizing an amount of movement needed to position and/or orient the intraoral adapter in order to image the back molar regions.

Mounting Mechanism

In some cases, the intraoral adapter may further comprise a mounting mechanism. The mounting mechanism may be provided on or near the distal portion of the elongated housing. The mounting mechanism may be configured to couple the intraoral adapter to a mobile device comprising one or more cameras. The mounting mechanism may be configured to couple the mobile device to the intraoral adapter such that a longitudinal axis of the viewing channel is substantially aligned with an optical axis of the camera of the mobile device. The longitudinal axis of the viewing channel may extend from the distal portion of the elongated housing to the proximal portion of the elongated housing. The longitudinal axis may coincide with a central axis of the intraoral adapter that extends from a center of a first opening of the elongated housing to a center of a second opening of the elongated housing. The first opening of the elongated housing may be located at a distal portion of the elongated housing, and the second opening of the elongated housing may be located at a proximal portion of the elongated housing. The optical axis of the camera may correspond to an imaging axis that extends from the lens of the camera to the one or more intraoral regions of the subject's mouth. The imaging axis may be substantially orthogonal to the lens of the one or more cameras of the mobile device.

The mounting mechanism of the intraoral adapter may be configured to mechanically engage with a mobile device or a casing of the mobile device. The mounting mechanism may comprise an elastic band, a strap, a clamp, a hook, a magnet, a bracket, or a holder. The mounting mechanism may be configured to provide the mobile device in a fixed position and/or a fixed orientation relative to the elongated housing, an opening of the elongated housing, or a structural component of the elongated housing or intraoral adapter. In some cases, the mounting mechanism may be configured to adjust a position and/or an orientation of the mobile device relative to the elongated housing, an opening of the elongated housing, or a structural component of the elongated housing or intraoral adapter.

Adjustable Mechanism

In some embodiments, the elongated housing of the intraoral adapter may comprise an adjustable mechanism that permits an orientation between the proximal portion and the distal portion of the elongated housing to be adjusted. The orientation may comprise an angular displacement or a spatial displacement between the proximal portion and the distal portion of the elongated housing. The angular displacement may range from about 0 degrees to about 90 degrees.

In some cases, the elongated housing may comprise (1) a first sub-housing comprising the proximal portion and (2) a second sub-housing comprising the distal portion, wherein the first sub-housing and the second sub-housing are operably coupled to each other via the adjustable mechanism.

The adjustable mechanism may comprise a rotatable mechanism that is configured to permit an adjustment of an orientation between the first sub-housing and the second sub-housing. In some cases, the rotatable mechanism may comprise a hinge, a knob, a dial, a gear, or a lever.

FIG. 7A, FIG. 7B, FIG. 7C, FIG. 7D, FIG. 8, and FIG. 9 illustrate an intraoral adapter comprising an elongated housing 110 and an attachment mechanism 170 or a mounting mechanism 200. A mobile device 300 may be releasably coupled to the intraoral adapter via the attachment mechanism 170 or the mounting mechanism 200. The attachment mechanism 170 or the mounting mechanism 200 may be configured to releasably couple the mobile device 300 to the intraoral adapter such that a longitudinal axis of the viewing channel 150 is substantially aligned with an optical axis of one or more cameras of the mobile device 300. The optical axis of the one or more cameras of the mobile device 300 may be aligned with one or more intraoral regions of the subject's mouth when the flange 140 of the elongated housing 110 is positioned between a tooth portion and a gum portion of the subject's mouth.

As described above, in some cases the elongated housing 110 may comprise (1) a first sub-housing 111 comprising the proximal portion of the elongated housing 110 and (2) a second sub-housing 112 comprising the distal portion of the elongated housing 110. The first sub-housing 111 and the second sub-housing 112 may be operably coupled to each other via an adjustable mechanism 400. The adjustable mechanism 400 may comprise a rotatable mechanism that is configured to permit an adjustment of an orientation between the first sub-housing 111 and the second sub-housing 112. The orientation may comprise an angular displacement or a spatial displacement between the proximal portion and the distal portion of the elongated housing. The angular displacement may range from about 0 degrees to about 90 degrees.

Camera Optical Path Adjustment Using Mirrors

Figure 9:
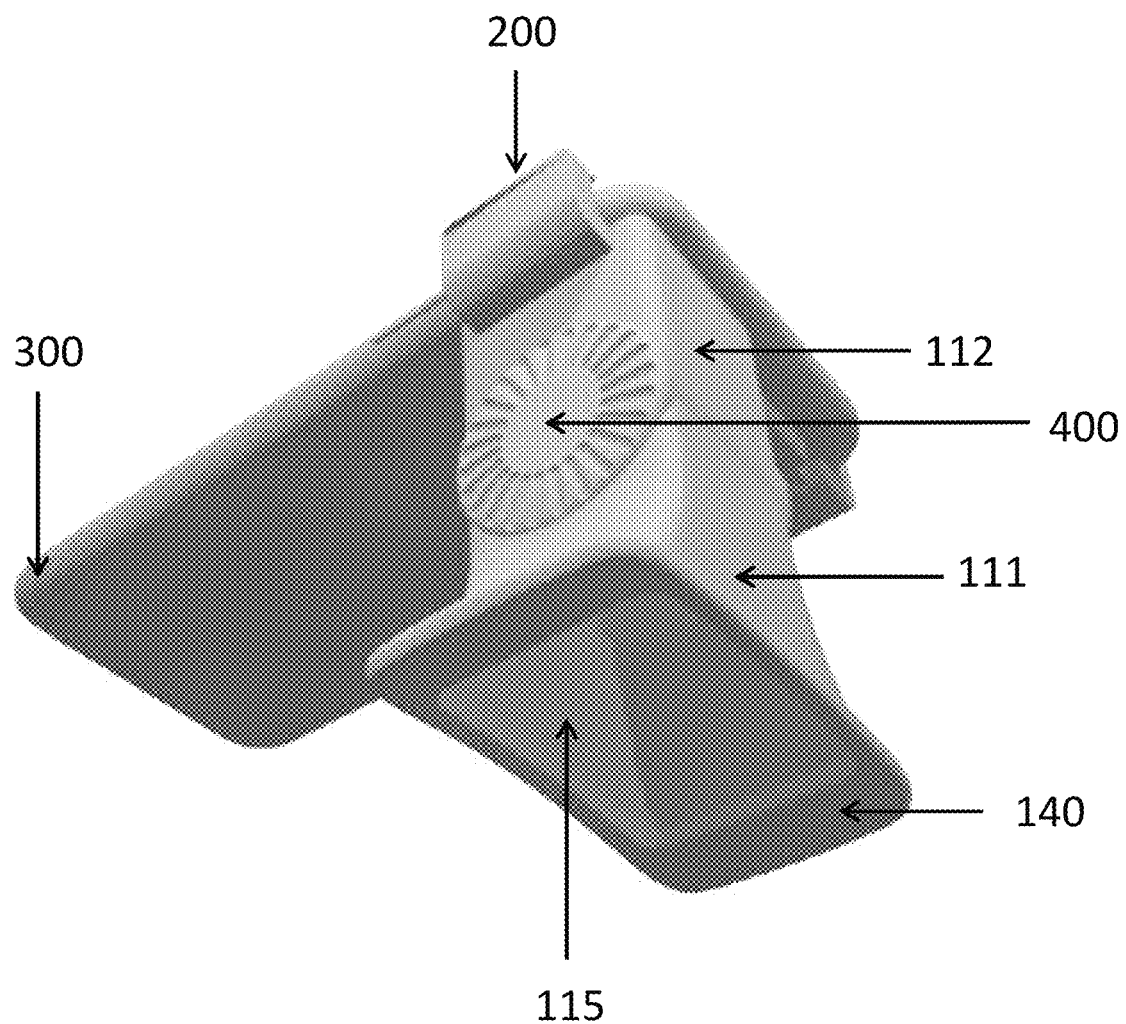

As shown in FIG. 9, the elongated housing of the intraoral adapter may comprise one or more internal surfaces 115. The one or more internal surfaces may form a spatial boundary defining a shape and/or a size of the viewing channel. In some cases, the one or more internal surfaces 115 may comprise a reflective surface. The reflective surface may comprise a mirror.

In some embodiments, the intraoral adapter may further comprise a mirror that is configured to adjust an optical path of the camera to enable the camera to capture one or more intraoral images of at least one of an upper dental arch and a lower dental arch of the subject. The mirror may be coupled to one or more internal surfaces of the elongated housing.

Figure 11:
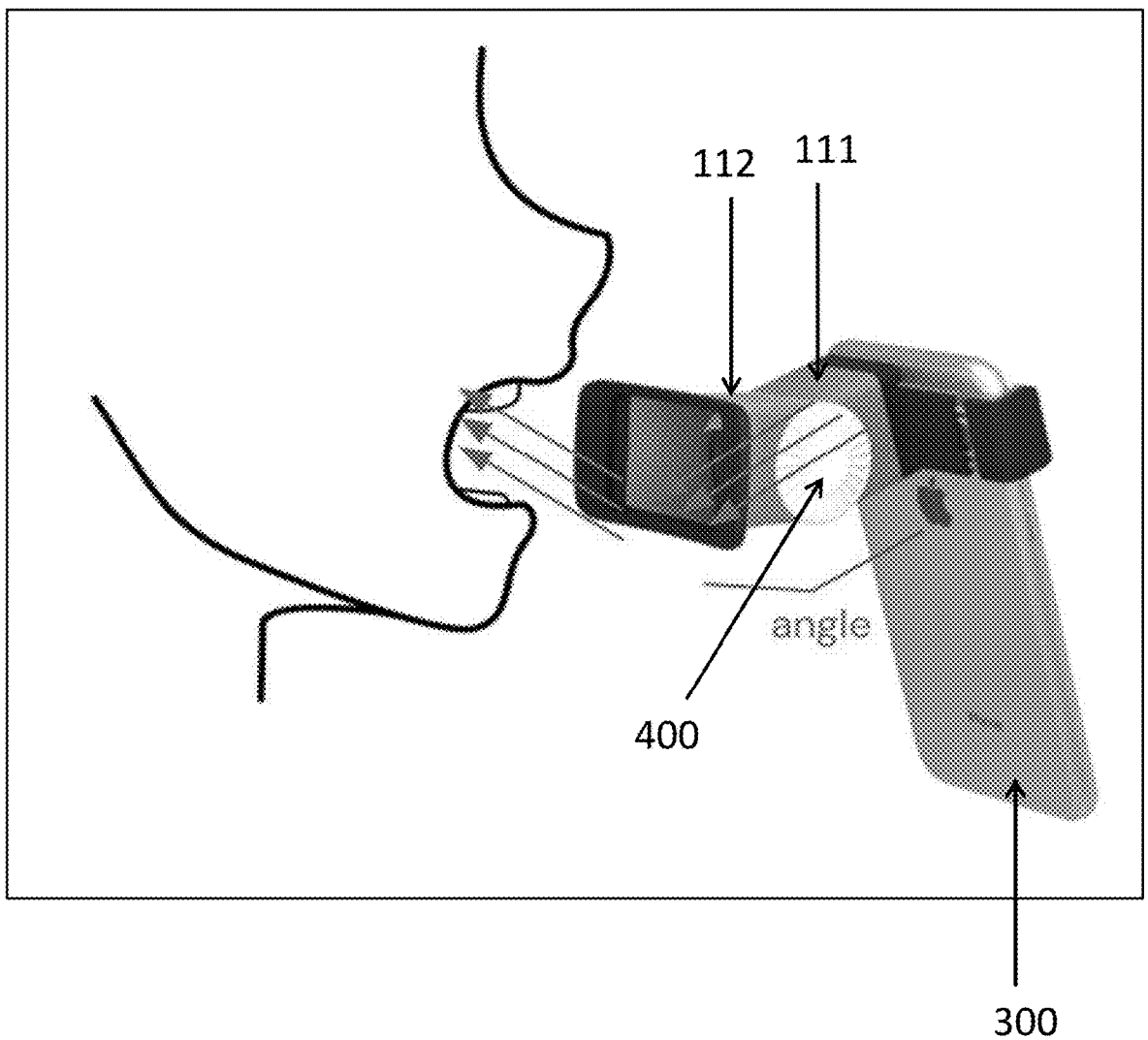
FIG. 11 schematically illustrates an adjustment mechanism configured to permit an orientation between a proximal portion and a distal portion of the elongated housing to be adjusted, in accordance with some embodiments.

As shown in FIG. 11, the adjustable mechanism 400 may be used to adjust an orientation between a first sub-housing 111 comprising the proximal portion of the elongated housing and a second sub-housing 112 comprising the distal portion of the elongated housing. As described above, in some cases, at least one internal surface of the first sub-housing 111 or the second sub-housing 112 may comprise a reflective surface. Adjusting the orientation between the first sub-housing 111 and the second sub-housing 112 may permit the camera to capture one or more intraoral images of an upper dental arch or a lower dental arch of the subject. When the adjustable mechanism is used to provide an angular displacement between the first sub-housing 111 and the second sub-housing 112, the reflective surface of the first sub-housing 111 or the second sub-housing 112 may be configured to adjust an optical path of the camera of the mobile device. In such cases, the camera of the mobile device may be configured to capture one or more intraoral images using the reflective surface. The one or more intraoral images captured using the reflective surface may comprise (1) a top-down view of a lower dental arch of the subject and/or (2) a bottom-up view of an upper dental arch of the subject.

Figure 12A:
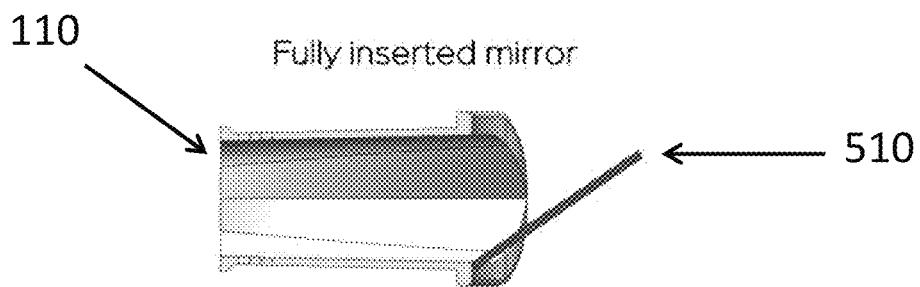
FIG. 12A, FIG. 12B, and FIG. 12C schematically illustrate a mirror that can be configured to adjust an optical axis of a camera of a mobile device, in accordance with some embodiments.

In some embodiments, the intraoral adapter may comprise an insertable mirror that is coupled to the elongated housing. FIG. 12A shows an intraoral adapter comprising an insertable mirror 510 that is coupled to elongated housing 110. In some cases, the insertable mirror 510 may be releasably coupled to the elongated housing 110. In some cases, the insertable mirror 510 may be coupled to the flange of the elongated housing 110. The insertable mirror 510 may be provided at an angular orientation relative to a longitudinal axis of the elongated housing 110. The angular orientation may comprise an angle that ranges between about 0 degrees to about 45 degrees. The insertable mirror 510 may be configured to adjust an optical path of the camera to enable the camera to capture one or more intraoral images of at least a portion of an upper dental arch or a lower dental arch of the subject.

Figure 12B:
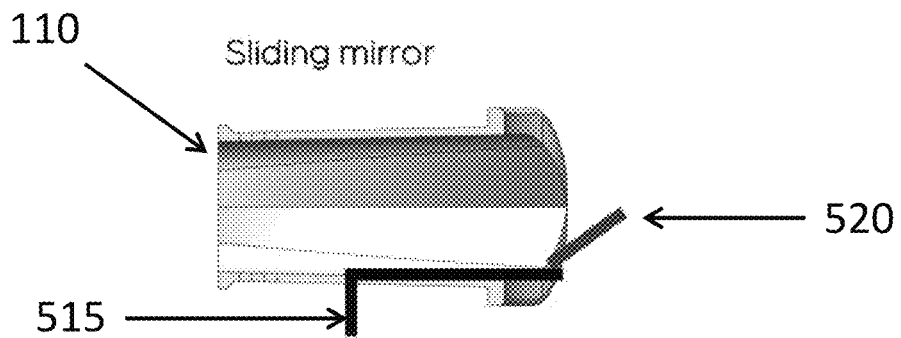

In some embodiments, the intraoral adapter may comprise a sliding mechanism and a mirror that is coupled to the sliding mechanism. FIG. 12B shows an intraoral adapter comprising a sliding mechanism 515 that is coupled to a mirror 520. The sliding mechanism 515 may be configured to engage with a portion of the elongated housing 110 so that a subject may use the sliding mechanism 515 to adjust a position or an orientation of the mirror 520 relative to one or more portions of the elongated housing 110 (e.g., an opening of the elongated housing or a flange of the elongated housing). In some cases, the sliding mechanism 515 may be configured to adjust a position or an orientation of the mirror 520 relative to one or more intraoral regions of the subject's mouth. The mirror 520 may be configured to adjust an optical path of the camera to enable the camera to capture one or more intraoral images of at least a portion of an upper dental arch or a lower dental arch of the subject. The mirror 520 may be provided at an angular orientation relative to a longitudinal axis of the elongated housing 110. The angular orientation may comprise an angle that ranges between about 0 degrees to about 45 degrees. The sliding mechanism 515 may be configured to adjust a distance between the mirror 520 and one or more intraoral regions of the subject's mouth. The sliding mechanism 515 may be configured to adjust a distance between the mirror 520 and one or more portions of the elongated housing 110 (e.g., an opening of the elongated housing or a flange of the elongated housing).

Figure 12C:
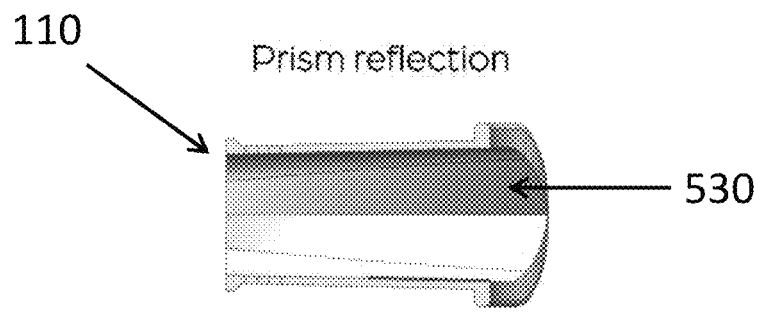

In some embodiments, the elongated housing of the intraoral adapter may comprise one or more internal surfaces of the elongated housing. FIG. 12C illustrates an intraoral adapter with an elongated housing 110 comprising a reflective surface. The reflective surface may correspond to an internal surface of the elongated housing 110. The reflective surface may comprise a mirror. The reflective surface may be configured to adjust an optical path of the camera to enable the camera to capture one or more intraoral images or videos of at least a portion of an upper dental arch or a lower dental arch of the subject. In some cases, the elongated housing 110 may comprise a plurality of reflective surfaces. The plurality of reflective surfaces may correspond to one or more internal surfaces of the elongated housing 110.

Imaging System

In another aspect, the present disclosure provides an intraoral imaging system. The intraoral imaging system may comprise an intraoral adapter as described elsewhere herein. The intraoral adapter may be operably coupled to a mobile device having one or more cameras. The intraoral imaging system may further comprise an image processing unit configured to (i) process a plurality of intraoral images or videos captured using the camera of the mobile device, and (ii) determine a dental condition of the subject based at least in part on the plurality of intraoral images or videos.

In some cases, the image processing unit may be located onboard the mobile device. In other cases, the image processing unit may be located on one or more servers that are remote from the mobile device.

The image processing unit may be configured to process a plurality of intraoral images. The plurality of intraoral images may be captured using a camera of a mobile device. Processing the plurality of intraoral images may comprise comparing a first set of pixel values within an intraoral image to a second set of pixel values within the intraoral image. The pixel values may comprise a value corresponding to a color or a brightness of one or more pixels. In some cases, processing the plurality of intraoral images may comprise comparing one or more pixel values within an intraoral image to a set of reference pixel values within a reference image. The set of reference pixel values may be accessed through a database that is located remote from a mobile device of a user. In some cases, the set of reference pixel values may indicate a certain dental condition (e.g., a presence of plaque or a presence of cavities). In some cases, processing the plurality of intraoral images may comprise comparing a first intraoral image to a second intraoral image. Comparing a first intraoral image to a second intraoral image may comprise tracking a movement of one or more features that are visible within the first intraoral image and the second intraoral image. Comparing a first intraoral image to a second intraoral image may comprise tracking a change in a shape of a subject's dental arches between the first intraoral image and the second intraoral image. In some cases, comparing a first intraoral image to a second intraoral image may comprise tracking a change in one or more pixel values between the first intraoral image and the second intraoral image. In some cases, the first intraoral image and the second intraoral image may be obtained within a single scanning session. In some cases, the first intraoral image may be obtained during a first scanning session and the second intraoral image may be obtained during a second scanning session that is initiated after the first scanning session.

The image processing unit may be configured to determine a dental condition of the subject based at least in part on the plurality of intraoral images captured using the camera of the mobile device. The dental condition may comprise (i) a movement of one or more teeth of the subject, (ii) an accumulation of plaque on the one or more teeth of the subject, (iii) a change in a color or a structure of the one or more teeth of the subject, (iv) a change in a color or a structure of a tissue adjacent to the one or more teeth of the subject, and/or (v) a presence or lack of presence of one or more cavities. In some cases, the plurality of intraoral images may be used to (i) predict a movement of one or more teeth of the subject, (ii) identify enamel wear patterns, (iii) create or modify a dental treatment plan, or (iv) generate or update an electronic medical record associated with a dental condition of the subject.

In some cases, the image processing unit may be configured to generate a three-dimensional (3D) model or a point cloud representation of a dental structure of the subject based at least in part on the plurality of intraoral images or videos. The three-dimensional model may be generated by overlaying and/or combining two or more intraoral images or image frames of the intraoral videos. In some cases, the three-dimensional model may be provided in an STL (Standard Triangle Language or Standard Tessellation Language) file format.

In some cases, the mobile device may comprise a stereoscopic camera. In such cases, the image processing unit of the intraoral imaging system may be configured to generate the three-dimensional model using one or more images obtained using the stereoscopic camera. In some cases, the mobile device may comprise a depth sensor. In such cases, the image processing unit of the intraoral imaging system may be configured to generate the three-dimensional model using depth information (e.g., a depth map) obtained using the depth sensor.

In some cases, the image processing unit may be configured to generate the three-dimensional model or the point cloud representation of the dental structure using one or more aspects of passive triangulation. Passive triangulation may involve using stereo-vision methods to generate a three-dimensional model based on a plurality of images obtained using a stereoscopic camera comprising two or more lenses. In other cases, the image processing unit may be configured to generate the three-dimensional model using one or more aspects of active triangulation. Active triangulation may involve using a light source (e.g., a laser source) to project a plurality of optical features (e.g., a laser stripe, one or more laser dots, a laser grid, or a laser pattern) onto one or more intraoral regions of a subject's mouth. Active triangulation may involve computing and/or generating a three-dimensional representation of the one or more intraoral regions of the subject's mouth based on a relative position or a relative orientation of each of the projected optical features in relation to one another. Active triangulation may involve computing and/or generating a three-dimensional representation of the one or more intraoral regions of the subject's mouth based on a relative position or a relative orientation of the projected optical features in relation to the light source or a camera of the mobile device.

In some cases, the image processing unit may be configured to generate the three-dimensional (3D) model or the point cloud representation of the dental structure based at least in part on an initial clinical scan of one or more intraoral regions of interest in the subject's mouth. The initial clinical scan may comprise an initial three-dimensional (3D) model or point cloud representation of the subject's dental structure that is generated before the plurality of intraoral images or videos are captured using the camera of the mobile device.

In some cases, the three-dimensional (3D) model or the point cloud representation of the subject's dental structure may be generated based at least in part on motion data associated with a movement of the intraoral adapter relative to one or more intraoral regions of interest. The motion data may be obtained using a motion sensor (e.g., an inertial measurement unit, an accelerometer, or a gyroscope).

The image processing unit may be configured to determine a dental condition of the subject based at least in part on the three-dimensional model or the point cloud representation of the subject's dental structures or dental features. The dental condition may comprise (i) a movement of one or more teeth of the subject, (ii) an accumulation of plaque on the one or more teeth of the subject, (iii) a change in a color or a structure of the one or more teeth of the subject, (iv) a change in a color or a structure of a tissue adjacent to the one or more teeth of the subject, and/or (v) a presence or lack of presence of one or more cavities. In some cases, the three-dimensional model may be used to (i) predict a movement of one or more teeth of the subject, (ii) identify enamel wear patterns, (iii) create or modify a dental treatment plan, or (iv) generate or update an electronic medical record associated with a dental condition of the subject.

Figure 13:
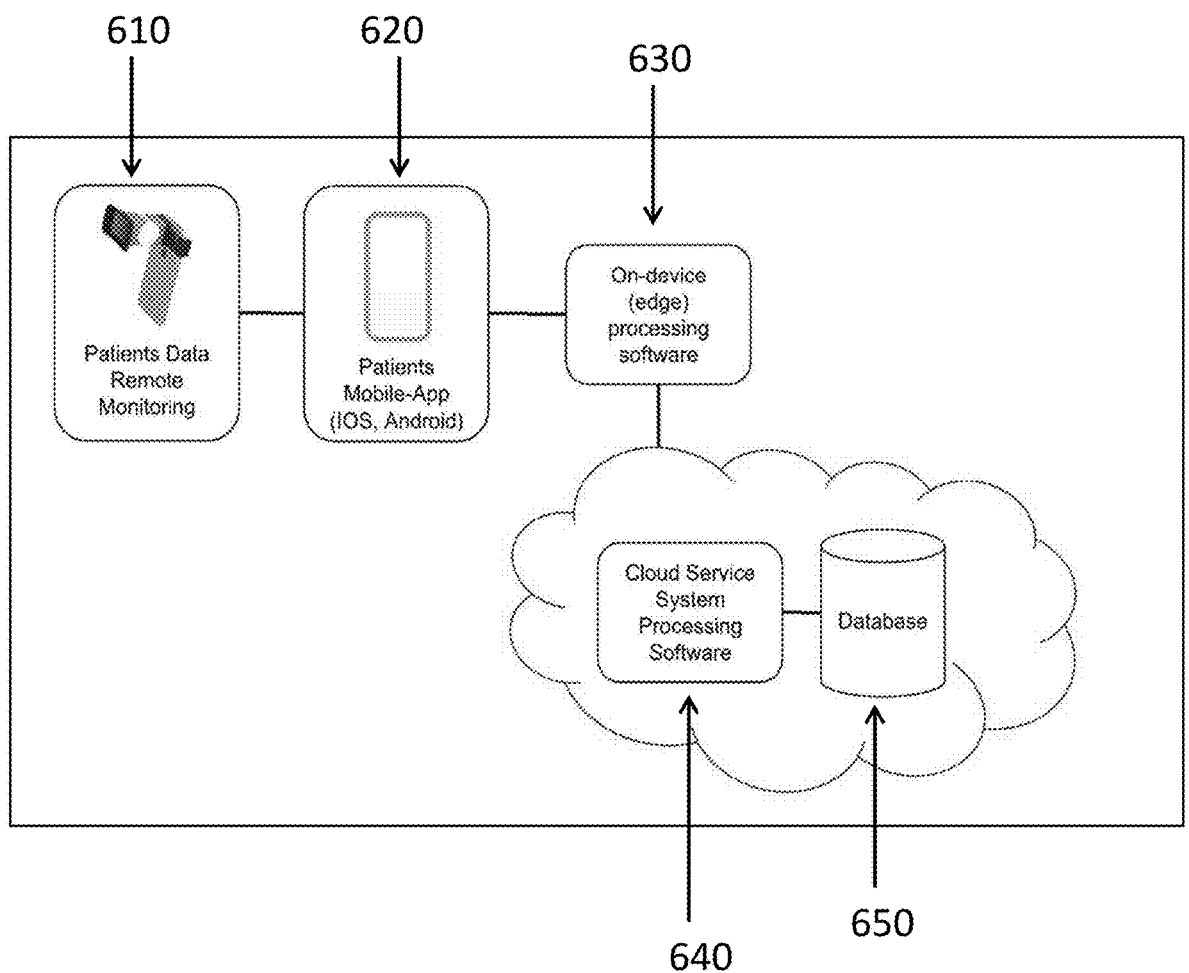
FIG. 13 schematically illustrates a system architecture of an intraoral imaging system, in accordance with some embodiments.

FIG. 13 illustrates a system architecture diagram corresponding to an operation and an implementation of the intraoral imaging systems and methods of the present disclosure. The system architecture may comprise a mobile device 610 coupled to an intraoral adapter. The system architecture may further comprise a mobile application 620 that may be installed on the mobile device 610. The mobile application 620 may be configured to perform one or more intraoral scans using a camera of the mobile device 610. The one or more intraoral scans may comprise one or more intraoral images or videos taken using the camera of the mobile device 610. In some cases, the system architecture may comprise processing software 630 located on the mobile device 610. The processing software 630 may be configured to process one or more intraoral images as described above. In some cases, the system architecture may comprise cloud processing software 640. The cloud processing software 640 may be implemented using one or more servers located remote from the mobile device 610. The cloud processing software 640 may be configured to process one or more intraoral images or videos as described above. In some cases, the cloud processing software 640 may be configured to process the one or more intraoral images or videos using data provided in a database 650. The database 650 may comprise data to aid in the processing of the one or more intraoral images. In some cases, the data may be usable by the cloud processing software 640 to identify one or more dental conditions of the subject based on the one or more intraoral images or videos captured using the camera of the subject's mobile device. In some cases, the database 650 may be configured to store one or more outputs generated by the cloud processing software 640. The one or more outputs may comprise a three-dimensional model or a point cloud representation of the subject's dental structure, or a quantitative and/or qualitative determination of one or more dental conditions of the subject.

In another aspect, the present disclosure provides a method for intraoral imaging. The method may comprise (a) providing an intraoral adapter as described herein. The method may further comprise (b) using the mounting mechanism to couple the distal portion of the elongated housing of the intraoral adapter to the mobile device. The method may further comprise (c) using the flange to couple the proximal portion of the elongated housing of the intraoral adapter to the subject's mouth. The method may further comprise (d) using the camera of the mobile device to image the intraoral region of the subject's mouth through the viewing channel of the intraoral adapter. As used herein, intraoral imaging may comprise obtaining one or more images and/or one or more videos of an intraoral region or one or more dental features in the intraoral region.

Figure 14:
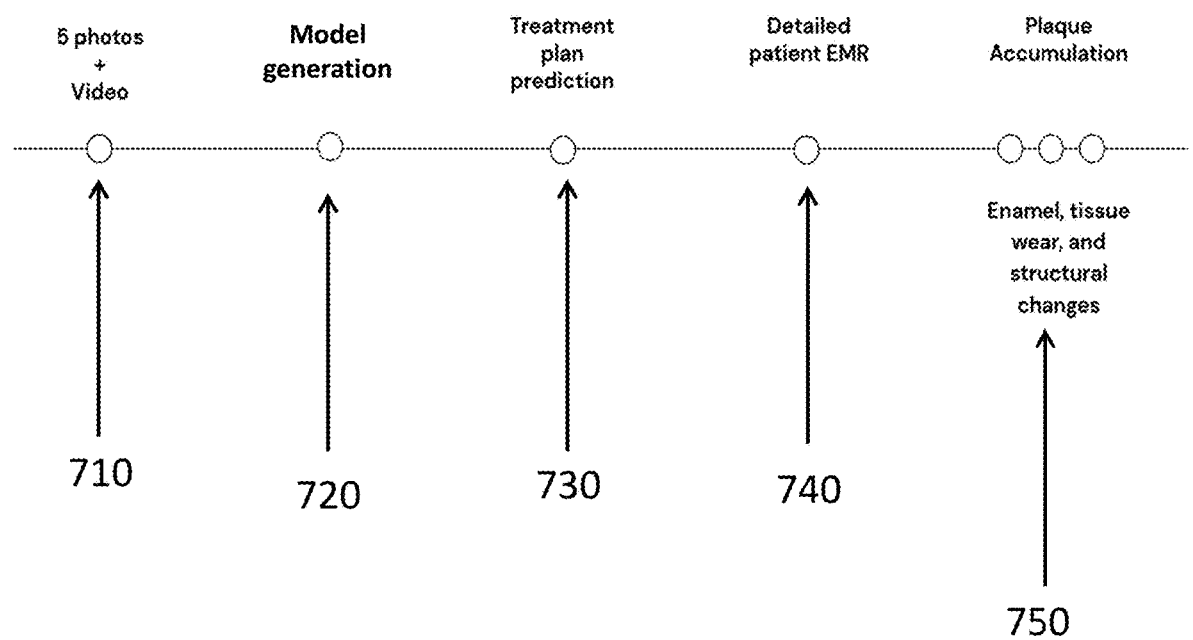
FIG. 14 schematically illustrates a plurality of applications based on a processing of intraoral images and/or intraoral videos, in accordance with some embodiments.

FIG. 14 illustrates a plurality of applications based on an acquisition of one or more intraoral images or intraoral videos 710 using the intraoral adapters and/or the intraoral imaging systems provided by the present disclosure. The intraoral adapters and/or the intraoral imaging systems provided herein may be used to obtain a plurality of intraoral images and/or an intraoral video 710 of one or more intraoral regions of a subject's mouth. In some cases, the plurality of intraoral images may comprise at least five or more intraoral images. In some cases, an image processing unit of the intraoral imaging system may be used to generate a three-dimensional model or point cloud representation 720 of the subject's dental structure based on the plurality of intraoral images and/or the intraoral video. In some non-limiting embodiments, the three-dimensional model or point cloud representation 720 may comprise an STL file. Alternatively, the three-dimensional model or point cloud representation 720 may not or need not comprise an STL file. In some cases, the imaging processing unit may be configured to generate, update, and/or predict a treatment plan 730 for the subject based on the three-dimensional model or point cloud representation 720 of the subject's dental structure and/or the plurality of intraoral images and the intraoral video 710. In some cases, the three-dimensional model or point cloud representation 720 of the subject's dental structure, the plurality of intraoral images and the intraoral video 710, and/or the predicted treatment plan 730 for the subject may be used to update an electronic medical record (EMR) 740 associated with the subject. In some cases, the plurality of intraoral images and the intraoral video 710, the three-dimensional model or point cloud representation 720 of the subject's dental structure, the predicted treatment plan 730, and/or the updated electronic medical record 740 may be used to evaluate a dental condition 750 indicating an accumulation of plaque on the subject's teeth, enamel wear, tissue wear, or any structural changes to the subject's dental structure.

Figure 15:
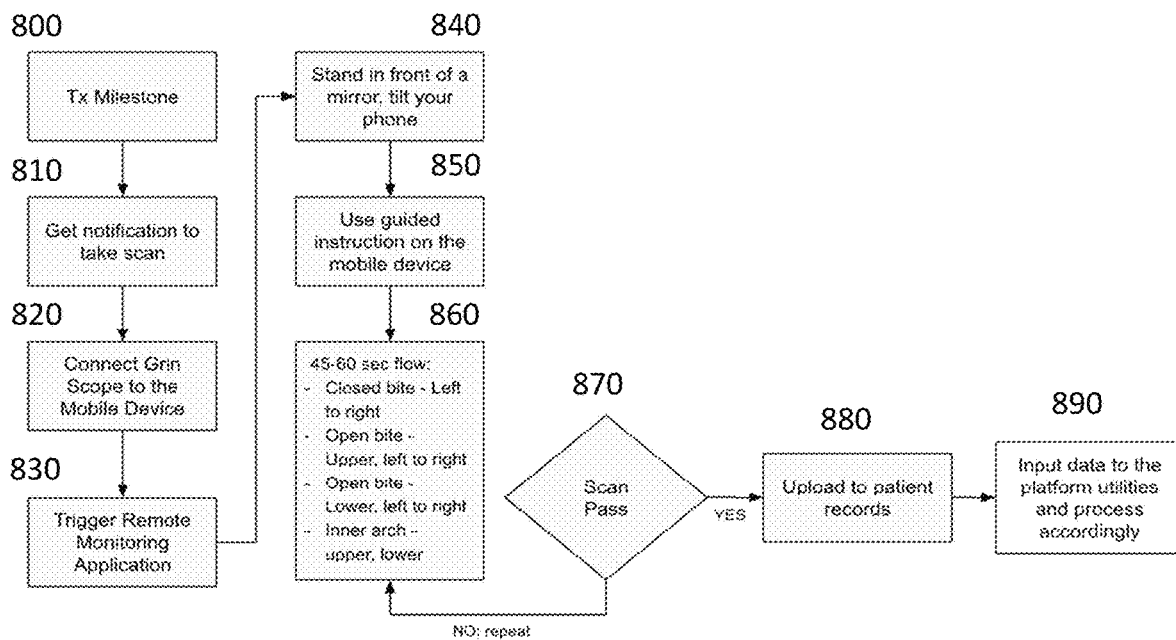
FIG. 15 schematically illustrates an exemplary method for remote dental monitoring, in accordance with some embodiments.

FIG. 15 illustrates another exemplary method for intraoral imaging. First, a subject may reach a patient-specific milestone associated with a dental treatment (800). The patient-specific milestone may be associated with a patient-specific treatment timeline. Next, the intraoral imaging system may provide the subject with a notification to take an intraoral scan (810). Next, the subject may connect a mobile device to an intraoral adapter (820). Next, the subject may use the mobile device to initiate an intraoral scan (830). Next, the mobile device may provide one or more instructions for the subject to stand in front of a mirror and to adjust a position and/or an orientation of the mobile device to take one or more intraoral scans (840). Next, the mobile device may provide guided instructions for the subject to take one or more intraoral scans (850). Next, the subject may take a plurality of intraoral scans (860). The plurality of intraoral scans may comprise a left to right or a right to left movement of the intraoral adapter while the subject has a closed bite. The plurality of intraoral scans may comprise a left to right or a right to left movement of the intraoral adapter while the subject has an open bite. The plurality of intraoral scans may comprise one or more scans of an upper dental arch and/or a lower dental arch of the subject. Next, the mobile device (or an application on the mobile device) may assess whether or not the intraoral scans are acceptable, based on lens cleanliness, image clarity, sufficient focus, centering of the intraoral images, and/or whether the subject has achieved a full occlusion capture including internal edges of a left dental arch, a right dental arch, a top dental arch, and/or a bottom dental arch (870). The guided instructions provided by the mobile device may comprise visual, textual, and/or audio guidance to aid the subject in capturing the one or more intraoral scans. The visual and textual guidance may be provided on a display of the subject's mobile device and may be viewed by the subject (e.g., by using a reflected mirror image that is visible to the subject when the subject is positioned in front of a mirror or another reflective surface). The audio guidance may be transmitted via a speaker of the subject's mobile device or via an audio output device in wired or wireless communication with the subject's mobile device.

If an intraoral scan is not acceptable, the subject may be prompted to perform another intraoral scan. If the intraoral scan is acceptable, the mobile device may upload the intraoral scan to a patient's electronic medical record (880). Next, an image processing unit may process the intraoral scan to determine a dental condition of the subject (890). The dental condition may comprise (i) a movement of one or more teeth of the subject, (ii) an accumulation of plaque on the one or more teeth of the subject, (iii) a change in a color or a structure of the one or more teeth of the subject, (iv) a change in a color or a structure of a tissue adjacent to the one or more teeth of the subject, and/or (v) a presence or lack of presence of one or more cavities. In some cases, the image processing unit may use the plurality of intraoral images to (i) predict a movement of one or more teeth of the subject, (ii) identify enamel wear patterns, (iii) create or modify a dental treatment plan, and/or (iv) generate or update an electronic medical record associated with a dental condition of the subject.

In some cases, the one or more intraoral scans captured by the subject may be provided to a practitioner or a caregiver. The practitioner or caregiver may be, for example, a dentist, an orthodontist, an oral surgeon, individuals having one or more dental specialties, dental staff, or any assistants, employees, or affiliates of such practitioners or caregivers. The one or more intraoral scans may be provided to the practitioner or caregiver, who may review the one or more intraoral scans and provide an assessment of a dental condition of the subject based on the one or more intraoral scans. In some cases, the assessment of the dental condition may comprise audio commentary as the practitioner reviews the one or more intraoral scans. The audio commentary may be provided alone or in combination with other forms of commentary (e.g., visual commentary or annotations). In some cases, the audio commentary may be transcribed, and the transcription of the audio commentary may be provided to the subject. In some cases, the assessment of the dental condition may comprise a video recording or a live stream of the practitioner providing the assessment. In some cases, the practitioner or caregiver may use the intraoral scans to update, modify, and/or change a patient-specific treatment timeline and/or the one or more treatment milestones and dates associated with the patient-specific treatment timeline. In some cases, the practitioner or caregiver may use the intraoral scans to update, modify, and/or change the subject's dental treatment plan.

Computer Systems

Figure 16:
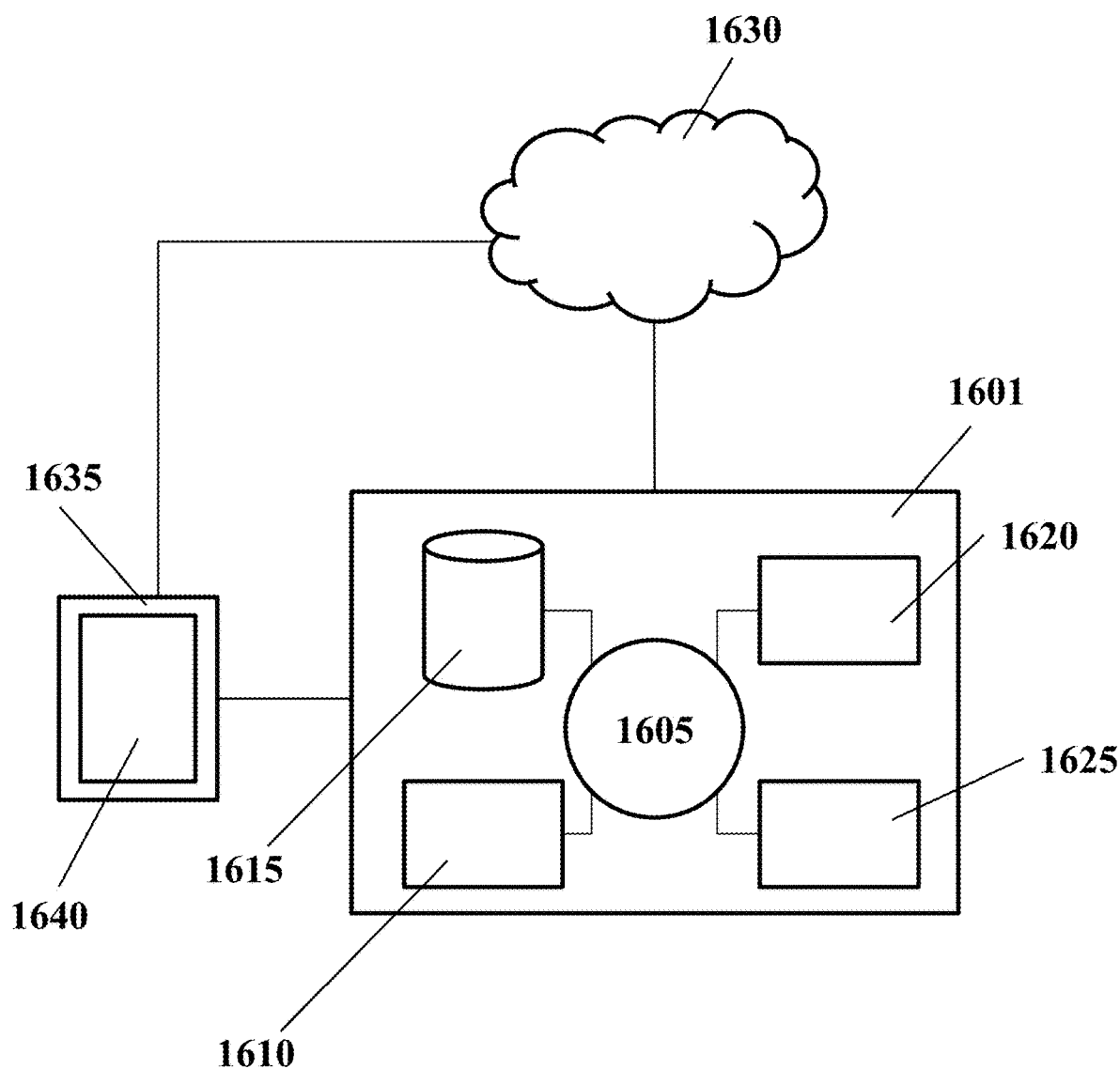
FIG. 16 schematically illustrates a computer system that is programmed or otherwise configured to implement methods provided herein.

In an aspect, the present disclosure provides computer systems that are programmed or otherwise configured to implement methods of the disclosure. FIG. 16 shows a computer system 1601 that is programmed or otherwise configured to implement a method for remote dental monitoring. The computer system 1601 may be configured to, for example, process a plurality of intraoral images captured using the camera of the mobile device, and determine a dental condition of the subject based at least in part on the plurality of intraoral images. The computer system 1601 may be configured to (i) predict a movement of one or more teeth of the subject, (ii) identify enamel wear patterns, (iii) create or modify a dental treatment plan, or (iv) generate or update an electronic medical record associated with the dental condition of the subject. The computer system 1601 may be configured to generate a three-dimensional (3D) model of a dental structure of the subject based at least in part on the plurality of intraoral images, and determine a dental condition of the subject based at least in part on the three-dimensional model. The computer system 1601 can be an electronic device of a user or a computer system that is remotely located with respect to the electronic device. The electronic device can be a mobile electronic device.

The computer system 1601 may include a central processing unit (CPU, also "processor" and "computer processor" herein) 1605, which can be a single core or multi core processor, or a plurality of processors for parallel processing. The computer system 1601 also includes memory or memory location 1610 (e.g., random-access memory, read-only memory, flash memory), electronic storage unit 1615 (e.g., hard disk), communication interface 1620 (e.g., network adapter) for communicating with one or more other systems, and peripheral devices 1625, such as cache, other memory, data storage and/or electronic display adapters. The memory 1610, storage unit 1615, interface 1620 and peripheral devices 1625 are in communication with the CPU 1605 through a communication bus (solid lines), such as a motherboard. The storage unit 1615 can be a data storage unit (or data repository) for storing data. The computer system 1601 can be operatively coupled to a computer network ("network") 1630 with the aid of the communication interface 1620. The network 1630 can be the Internet, an internet and/or extranet, or an intranet and/or extranet that is in communication with the Internet. The network 1630 in some cases is a telecommunication and/or data network. The network 1630 can include one or more computer servers, which can enable distributed computing, such as cloud computing. The network 1630, in some cases with the aid of the computer system 1601, can implement a peer-to-peer network, which may enable devices coupled to the computer system 1601 to behave as a client or a server.

The CPU 1605 can execute a sequence of machine-readable instructions, which can be embodied in a program or software. The instructions may be stored in a memory location, such as the memory 1610. The instructions can be directed to the CPU 1605, which can subsequently program or otherwise configure the CPU 1605 to implement methods of the present disclosure. Examples of operations performed by the CPU 1605 can include fetch, decode, execute, and writeback.

The CPU 1605 can be part of a circuit, such as an integrated circuit. One or more other components of the system 1601 can be included in the circuit. In some cases, the circuit is an application specific integrated circuit (ASIC).

The storage unit 1615 can store files, such as drivers, libraries and saved programs. The storage unit 1615 can store user data, e.g., user preferences and user programs. The computer system 1601 in some cases can include one or more additional data storage units that are located external to the computer system 1601 (e.g., on a remote server that is in communication with the computer system 1601 through an intranet or the Internet).

The computer system 1601 can communicate with one or more remote computer systems through the network 1630. For instance, the computer system 1601 can communicate with a remote computer system of a user (e.g., a subject, a dental patient, or a dentist). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 1601 via the network 1630.

Methods as described herein can be implemented by way of machine (e.g., computer processor) executable code stored on an electronic storage location of the computer system 1601, such as, for example, on the memory 1610 or electronic storage unit 1615. The machine executable or machine readable code can be provided in the form of software. During use, the code can be executed by the processor 1605. In some cases, the code can be retrieved from the storage unit 1615 and stored on the memory 1610 for ready access by the processor 1605. In some situations, the electronic storage unit 1615 can be precluded, and machine-executable instructions are stored on memory 1610.

The code can be pre-compiled and configured for use with a machine having a processor adapted to execute the code, or can be compiled during runtime. The code can be supplied in a programming language that can be selected to enable the code to execute in a pre-compiled or as-compiled fashion.

Aspects of the systems and methods provided herein, such as the computer system 1601, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media including, for example, optical or magnetic disks, or any storage devices in any computer(s) or the like, may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 1601 can include or be in communication with an electronic display 1635 that comprises a user interface (UI) 1640 for providing, for example, a portal for a subject or a dental patient to view one or more intraoral images captured using a mobile device of the subject or the dental patient. In some cases, the user interface may provide a portal for a subject or a dental patient to view one or more three-dimensional models of the subject's or dental patient's dental structure generated based on the one or more intraoral images captured using the mobile device. In some cases, the user interface may provide a portal for a subject or a dental patient to view one or more treatment plans generated based on the one or more intraoral images and/or the one or more three-dimensional models of the subject's dental structure. The portal may be provided through an application programming interface (API). A user or entity can also interact with various elements in the portal via the UI. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 1605. The algorithm can, for example, implement a method for remote dental monitoring. The method may comprise processing a plurality of intraoral images captured using the camera of the mobile device, and determining a dental condition of the subject based at least in part on the plurality of intraoral images. In some cases, the method may comprise (i) predicting a movement of one or more teeth of the subject, (ii) identifying enamel wear patterns, (iii) creating or modifying a dental treatment plan, or (iv) generating or updating an electronic medical record associated with the dental condition of the subject, based at least in part on the plurality of intraoral images. In some cases, the method may comprise using the intraoral images to generate a three-dimensional (3D) model of a dental structure of the subject, and determining a dental condition of the subject based at least in part on the three-dimensional model.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. An intraoral imaging system comprising:
an intraoral adapter comprising:
an elongated housing comprising a viewing channel between a proximal portion and a distal portion of the elongated housing, wherein a cross-sectional width at opposing ends of the elongated housing gradually increases from the distal portion to the proximal portion thereby resulting in an exterior surface of the elongated housing having an outward sloping profile, wherein the viewing channel defines a field of view of an intraoral region of a subject's mouth, wherein a cross-sectional shape of the viewing channel is different at the opposing ends of the elongated housing; and
a mount for coupling the intraoral adapter to a mobile device comprising a camera, wherein the mount is located on the distal portion of the elongated housing and configured to couple the mobile device to the intraoral adapter such that a longitudinal axis of the viewing channel is substantially aligned with an optical axis of the camera of the mobile device,
wherein the elongated housing comprises a flange for coupling the intraoral adapter to the subject's mouth, wherein the flange is positioned entirely outside the field of view of the intraoral region of the subject's mouth, and wherein the intraoral adapter is configured to (i) permit or enable a movement or an adjustment of the intraoral adapter relative to a plurality of intraoral regions of interest, and (ii) capture full occlusion views and full lateral views of the subject in one or more scans; and
a dental monitoring system configured to (i) notify the subject to capture the one or more scans using the intraoral adapter and (ii) assess or review a quality of the one or more scans before providing the one or more scans to a dental practitioner or an image processing unit.

2. The intraoral imaging system of claim 1, wherein the one or more scans indicate a dental condition of the subject, wherein the dental condition comprises (i) a movement of one or more teeth of the subject, (ii) an accumulation of plaque on the one or more teeth of the subject, (iii) a change in a color or a structure of the one or more teeth of the subject, (iv) a change in a color or a structure of a tissue adjacent to the one or more teeth of the subject, and/or (v) a presence or lack of presence of one or more cavities.

3. The intraoral imaging system of claim 1, wherein the one or more scans comprise a plurality of intraoral images or videos, wherein the plurality of intraoral images or videos are usable to (i) predict a movement of one or more teeth of the subject, (ii) identify enamel wear patterns, (iii) create or modify a dental treatment plan, or (iv) generate or update an electronic medical record associated with the dental condition of the subject.

4. The intraoral imaging system of claim 1, wherein the one or more scans are usable to assess the subject's actual progress in relation to a dental treatment plan based at least in part on a comparison of (i) one or more changes in a dental structure or dental condition of the subject and (ii) a planned or estimated change in the dental structure or the dental condition of the subject.

5. The intraoral imaging system of claim 1, wherein the dental monitoring system is configured to notify the subject to capture the one or more scans based on a timeline or a milestone associated with a dental treatment.

6. The intraoral imaging system of claim 1, wherein the dental monitoring system is configured to prompt the subject to retake a scan if the scan does not meet a threshold image or video quality.

7. The intraoral imaging system of claim 6, wherein the threshold image or video quality corresponds to at least one of image clarity, image focus, or image centering, and whether the subject has achieved a full occlusion capture including internal edges of a left dental arch, a right dental arch, a top dental arch, and/or a bottom dental arch.

8. The intraoral imaging system of claim 1, wherein the dental monitoring system is configured to provide the subject with feedback or commentary from the dental practitioner.

9. The intraoral imaging system of claim 8, wherein the feedback or commentary comprises one or more annotations to the one or more scans.

10. The intraoral imaging system of claim 1, wherein the dental monitoring system comprises a computer program or a mobile application comprising instructions executable by the mobile device to (i) notify the subject to capture the one or more scans and (ii) assess or review the quality of the one or more scans.

11. The intraoral imaging system of claim 1, wherein the dental monitoring system is configured to provide the subject with guidance or instructions for positioning or moving the intraoral adapter to capture the one or more scans.

12. The intraoral imaging system of claim 11, wherein the guidance or instructions comprise audio or visual prompts.

13. The intraoral imaging system of claim 1, wherein the flange extends peripherally around an opening at the proximal portion of the elongated housing.

14. The intraoral imaging system of claim 13, wherein the flange extends around at least a portion of the opening at the proximal portion of the elongated housing.

15. The intraoral imaging system of claim 1, wherein the flange extends outwards from a peripheral portion or a perimeter of the opening.

16. The intraoral imaging system of claim 1, wherein the flange does not extend into the viewing channel and does not block or occlude the field of view.

17. The intraoral imaging system of claim 1, wherein the flange permits or enables the imaging of the one or more intraoral regions of interest from a plurality of different angles or perspectives, wherein the plurality of different angles or perspectives comprise a front view, a side view, a bottom view, and a top view of the one or more intraoral regions of interest.

18. The intraoral imaging system of claim 1, wherein the flange permits or enables a movement or an adjustment of the intraoral adapter while the flange is positioned between a lip portion and a gum portion of the subject's mouth for imaging of one or more molar regions of the subject's mouth.

19. The intraoral imaging system of claim 1, wherein the flange is configured to be inserted into the intraoral region of the subject's mouth such that the flange is located between a lip portion and a gum portion of the subject's mouth.

20. The intraoral imaging system of claim 1, wherein the flange comprises a concave curvature that is configured to conform to a shape or a structure of a gum portion of the subject's mouth.

21. The intraoral imaging system of claim 1, wherein the field of view has (i) a circular or elliptical shape, (ii) a shape that comprises at least three or more sides, (iii) a hexagonal shape, (iv) a regular shape that comprises two or more sides with a same length, or (v) an irregular shape that comprises two or more sides with different lengths.

22. The intraoral imaging system of claim 1, wherein the mount is configured to mechanically engage with the mobile device or a casing of the mobile device using an elastic band, a strap, a clamp, a hook, a magnet, a bracket, or a holder.

23. The intraoral imaging system of claim 1, wherein the mount is detachable from the elongated housing.

24. The intraoral imaging system of claim 1, wherein the flange extends outwards from the exterior surface of the elongated housing at an angle of at least 15°.

25. The intraoral imaging system of claim 1, wherein the flange extends outwards from the exterior surface of the elongated housing at an angle of at least 45°.

26. The intraoral imaging system of claim 1, wherein the flange extends outwards from the elongated housing by at least 1 millimeter.

27. The intraoral imaging system of claim 1, wherein the flange extends outwards from the elongated housing by at least 5 millimeters.

28. The intraoral imaging system of claim 1, wherein the flange extends outwards from the elongated housing by a first width in a first direction, and wherein the flange extends outwards from the elongated housing by a second width in a second direction orthogonal to the first direction, wherein said second width is greater than first width.

29. The intraoral imaging system of claim 1, wherein the flange extends outwards from the elongated housing by at least 1 millimeter in a first direction, and wherein the flange extends outwards from the elongated housing by at least 5 millimeters in a second direction orthogonal to the first direction.

* * * * *